(12) United States Patent
Kawamura

(10) Patent No.: US 8,623,520 B2
(45) Date of Patent: Jan. 7, 2014

(54) FUSED AROMATIC DERIVATIVE AND ORGANIC ELECTROLUMINESCENCE DEVICE USING THE SAME

(75) Inventor: Masahiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 356 days.

(21) Appl. No.: 12/743,815

(22) PCT Filed: Nov. 17, 2008

(86) PCT No.: PCT/JP2008/070882
§ 371 (c)(1),
(2), (4) Date: Jul. 26, 2010

(87) PCT Pub. No.: WO2009/066641
PCT Pub. Date: May 28, 2009

(65) Prior Publication Data
US 2010/0295030 A1 Nov. 25, 2010

(30) Foreign Application Priority Data
Nov. 21, 2007 (JP) ................................. 2007-301837

(51) Int. Cl.
*H01L 51/54* (2006.01)
*C07C 15/38* (2006.01)

(52) U.S. Cl.
USPC ............... 428/690; 428/917; 585/26; 257/40; 313/504; 313/506

(58) Field of Classification Search
None
See application file for complete search history.

(56) References Cited

U.S. PATENT DOCUMENTS

| | | |
|---|---|---|
| 6,861,163 B2 | 3/2005 | Cheng et al. |
| 2004/0076852 A1 | 4/2004 | Cheng et al. |

(Continued)

FOREIGN PATENT DOCUMENTS

| | | |
|---|---|---|
| EP | 0 847 228 A2 | 6/1998 |
| EP | 1 553 154 A1 | 7/2005 |

(Continued)

OTHER PUBLICATIONS

Communication (Supplementary European Search Report) in EP Appln No. 08 85 1689 dated Dec. 28, 2010.

(Continued)

*Primary Examiner* — Dawn Garrett
(74) *Attorney, Agent, or Firm* — Foley & Lardner LLP

(57) ABSTRACT

A fused aromatic derivative shown by the following formula (1):

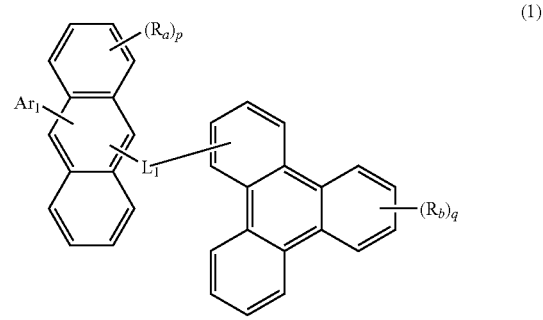

wherein $R_a$ and $R_b$ are independently a hydrogen atom or a substituent, p is an integer of 1 to 8 and q is an integer of 1 to 11, and when p and q are two or more, $R_a$s and $R_b$s may be independently the same or different, and adjacent substituents $R_a$s may form a ring, $L_1$ is a single bond or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that when $L_1$ is a single bond and at least one of $R_a$s is not a hydrogen atom, $Ar_1$ is not a triphenylenyl group, and provided that substituents of $L_1$ and $Ar_1$, and $R_a$ and $R_b$ contain no amino group.

14 Claims, 1 Drawing Sheet

(56) References Cited

U.S. PATENT DOCUMENTS

| | | |
|---|---|---|
| 2006/0043858 A1 | 3/2006 | Ikeda et al. |
| 2006/0204783 A1* | 9/2006 | Conley et al. ............ 428/690 |
| 2007/0252522 A1* | 11/2007 | Kondakov et al. .......... 313/506 |
| 2008/0182129 A1* | 7/2008 | Klubek et al. ............ 428/704 |
| 2010/0025661 A1 | 2/2010 | Wang et al. |
| 2011/0034744 A1 | 2/2011 | Ikeda et al. |
| 2011/0054228 A1* | 3/2011 | Kim et al. ................ 585/26 |
| 2012/0235561 A1 | 9/2012 | Ikeda et al. |

FOREIGN PATENT DOCUMENTS

| | | |
|---|---|---|
| EP | 2 108 689 A2 | 10/2009 |
| JP | 2003-109765 A | 4/2003 |
| JP | 2004-059535 A | 2/2004 |
| JP | 2004-139957 A | 5/2004 |
| JP | 2005-041843 | 2/2005 |
| JP | 2006-151844 A | 6/2006 |
| KP | 20070102243 A | 10/2007 |
| WO | WO 2004/018587 A1 | 3/2004 |
| WO | WO 2006/003842 A1 | 1/2006 |
| WO | WO 2008/094399 A1 | 8/2008 |
| WO | WO-2009/066809 A1 | 5/2009 |
| WO | WO-2009/099133 A1 | 8/2009 |

OTHER PUBLICATIONS

Office Action Japanese Patent Application No. 2009-542548 dated Jul. 9, 2013.
Communication Pursuant to Article 94(3)EPC EP Application No. 08 851 689.3 dated Jun. 27, 2013.

* cited by examiner

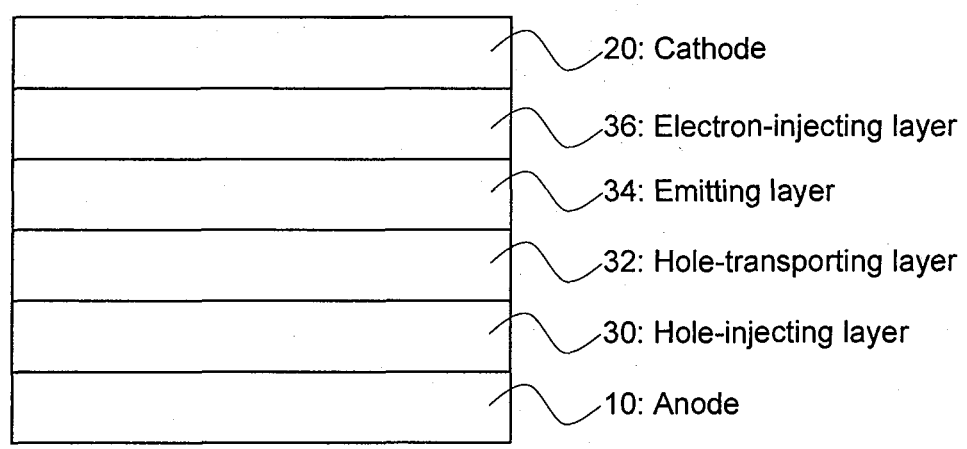

FUSED AROMATIC DERIVATIVE AND ORGANIC ELECTROLUMINESCENCE DEVICE USING THE SAME

TECHNICAL FIELD

The invention relates to a novel fused aromatic derivative which is useful as a material for an organic electroluminescence device, and an organic electroluminescence device using the same.

BACKGROUND ART

An organic electroluminescence device (hereinafter the term "electroluminescence" is often abbreviated as "EL") is a self-emission device utilizing the principle that an emission material emits light by the recombination energy of holes injected from an anode and electrons injected from a cathode when an electric field is impressed.

An organic EL device has made a remarkable progress. In addition, since an organic EL device has characteristics such as low voltage driving, high luminance, variety in emission wavelength, high response and capability of fabricating a thin and lightweight emitting device, its application to a wide range of fields is expected.

Emission materials used in an organic EL device have conventionally been studied actively since they influence largely the color of light emitted by a device or on emission life.

As the emission material, a chelate complex such as tris(8-quinolinolato)aluminum complex, a coumarin derivative, a tetraphenylbutadiene derivative, a bisstyrylarylene derivative and an oxadiazole derivative are known. By using such emission materials, emission in a visible range from blue to red can be obtained.

Use of a phosphorescent compound as an emission material for utilizing triplet energy for emission has been studied. For example, it is known that an organic EL device using an iridium complex as an emission material exhibits a high luminous efficiency.

An organic EL device using polyphenylene vinylene (PPV) as a conjugated polymer is known. In this device, PPV is applied and formed into a single film and this device is confirmed to emit light.

In Patent Document 1, an anthracene derivative is used as a material for an organic EL device.

In Patent Document 2, a compound having a triphenyl group is used as a material for an organic EL device.

In patent Document 3, an aminoanthryl derivative is used as a material for an organic EL device.

[Patent Document 1] JP-A-2004-59535
[Patent Document 2] JP-A-2004-139957
[Patent Document 3] JP-A-2006-151844

An object of the invention is to provide an organic material which is suitable for use as a material for an organic EL device.

DISCLOSURE OF THE INVENTION

The inventor(s) have found that a specific fused aromatic derivative having an anthracene structure and a triphenylene structure is effective for prolonging the lifetime, increasing the efficiency and lowering the voltage of an organic EL device. The invention has been made on this finding.

According to the invention, the following fused aromatic derivative or the like can be provided.

Embodiment 1. A fused aromatic derivative shown by the following formula (1):

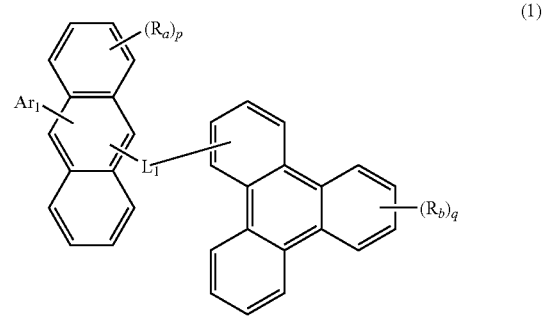

wherein $R_a$ and $R_b$ are independently a hydrogen atom or a substituent, p is an integer of 1 to 8, and q is an integer of 1 to 11, when p or q is 2 or more, $R_a$s or $R_b$s may be independently the same or different, and adjacent substituents $R_a$s may form a ring, $L_1$ is a single bond, or a substituted or unsubstituted divalent linking group, and $Ar_1$ is a substituted or unsubstituted aryl group having 6 to 50 carbon atoms that form a ring (hereinafter referred to as "ring carbon atoms") or a substituted or unsubstituted heteroaryl group having 5 to 50 atoms that form a ring (hereinafter referred to as "ring atoms"), provided that when the triphenylene group bonds to the 9th or 10th position of the anthracene skeleton, $L_1$ is a single bond and at least one of $R_a$s is not a hydrogen, $Ar_1$ is not a triphenylenyl group, and provided that substituents of $L_1$ and $Ar_1$ and $R_a$ and $R_b$ contain no amino group.

Embodiment 2. The fused aromatic derivative according to Embodiment 1, which is shown by the following formula (1):

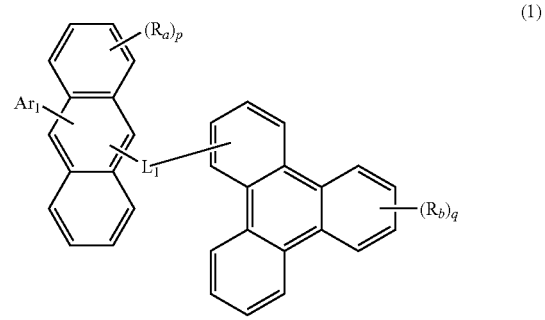

wherein $R_a$ and $R_b$ are independently a hydrogen atom or a substituent, p is an integer of 1 to 8, and q is an integer of 1 to 11, when p or q is two or more, $R_a$s or $R_b$s may be independently the same or different, and adjacent substituents $R_a$s may form a ring, $L_1$ is a single bond or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that when $L_1$ is a single bond and at least one of $R_a$s is not a hydrogen atom, $Ar_1$ is not a triphenylenyl group, and provided that substituents of $L_1$ and $Ar_1$ and $R_a$ and $R_b$ contain no amino group.

Embodiment 3. The fused aromatic derivative according to Embodiment 1 or 2, which is shown by the following formula (2):

(2)

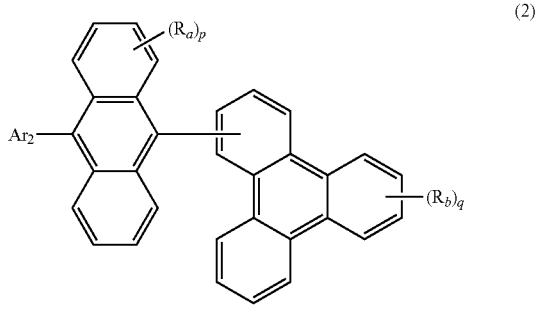

wherein $R_a$, $R_b$, p and q are the same as in the formula (1), and $Ar_2$ is a substituted or unsubstituted aryl group having 6 to 50 ring carbon atoms, provided that when at least one of $R_a$s is not a hydrogen atom, $Ar_2$ is not a triphenylenyl group.

Embodiment 4. The fused aromatic derivative according to Embodiment 3, wherein in the formula (2), $Ar_2$ is a substituted or unsubstituted fused aromatic ring having 10 to 20 ring carbon atoms.

Embodiment 5. The fused aromatic derivative according to Embodiment 1 or 2, which is shown by the following formula (3):

(3)

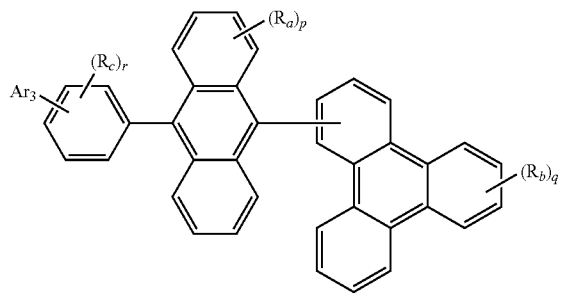

wherein $R_a$, $R_b$, p and q are the same as in the formula (1), $R_c$ is a hydrogen atom or substituent, and r is an integer of 1 to 4, and when r is two or more, $R_c$s may be the same or different, and $Ar_3$ is a substituted or unsubstituted aryl group having 6 to 50 ring carbon atoms or a substituted or unsubstituted heteroaryl group having 5 to 50 ring atoms.

Embodiment 6. The fused aromatic derivative according to Embodiment 5, wherein in the formula (3), $Ar_3$ is a substituted or unsubstituted fused aromatic ring having 10 to 20 ring carbon atoms.

Embodiment 7. The fused aromatic derivative according to Embodiment 1 or 2, which is shown by the following formula (4):

(4)

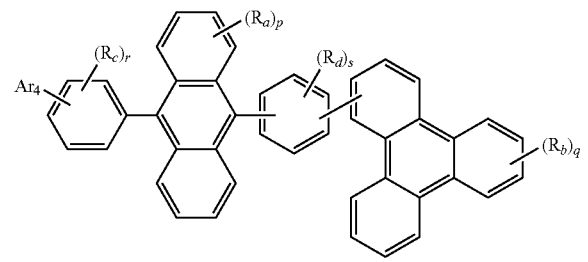

wherein $R_a$, $R_b$, p and q are the same as in the formula (1), $R_c$ and $R_d$ are independently a hydrogen atom or a substituent, r and s are independently an integer of 1 to 4, and when r or s is two or more, $R_c$s or $R_d$s are independently the same or different, and $Ar_4$ is a substituted or unsubstituted aryl group having 6 to 50 ring carbon atoms or a substituted or unsubstituted heteroaryl group having 5 to 50 ring atoms.

Embodiment 8. The fused aromatic derivative according to Embodiment 7, wherein in the formula (4), $Ar_4$ is a substituted or unsubstituted fused aromatic ring having 10 to 20 ring carbon atoms.

Embodiment 9. The fused aromatic derivative according to Embodiment 1 or 2, which is shown by the following formula (5):

(5)

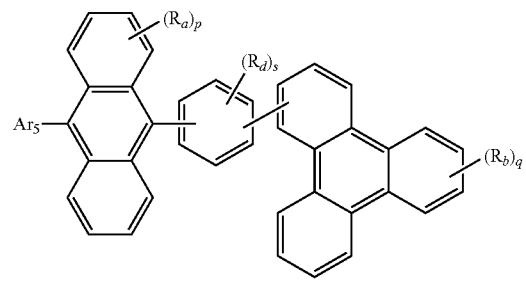

wherein $R_a$, $R_b$, p and q are the same as in the formula (1), $R_d$ is a hydrogen atom or a substituent, s an integer of 1 to 4, and when s is two or more, $R_d$s may be the same or different, and $Ar_5$ is a substituted or unsubstituted fused aromatic group having 10 to 50 ring carbon atoms.

Embodiment 10. The fused aromatic derivative according to Embodiment 9, wherein in the formula (5), $Ar_5$ is a substituted or unsubstituted naphthyl group.

Embodiment 11. A material for an organic electroluminescence device comprising the fused aromatic derivative according to any one of Embodiments 1 to 10.

Embodiment 12. The material for an organic electroluminescence derivative according to Embodiment 11, which is an emitting material.

Embodiment 13. An organic electroluminescence device comprising:

an anode, a cathode, and one or more organic thin film layers comprising an emitting layer between the anode and the cathode, wherein at least one of the organic thin film layers comprises the fused aromatic derivative according to any one of Embodiments 1 to 10.

Embodiment 14. The organic electroluminescence device according to Embodiment 13, wherein the emitting layer comprises the fused aromatic derivative.

Embodiment 15. The organic electroluminescence device according to Embodiment 14, wherein the emitting layer comprises the fused aromatic derivative as a host material.

Embodiment 16. The organic electroluminescence device according to any one of Embodiments 13 to 15, wherein the emitting layer further comprises at least one of a fluorescent dopant and a phosphorescent dopant.

Embodiment 17. The organic electroluminescence device according to Embodiment 16, wherein the fluorescent dopant is an arylamine compound.

Embodiment 18. The organic electroluminescence device according to Embodiment 16, wherein the fluorescent dopant is a styrylamine compound.

According to the invention, it is possible to provide a fused aromatic derivative suitable as a material for an organic EL device.

The organic EL device using the fused aromatic derivative of the invention has a long lifetime and a high efficiency, and is capable of being driven at a low voltage.

BRIEF DESCRIPTION OF THE DRAWINGS

FIG. 1 is a schematic cross-sectional view of the organic EL device according to one embodiment of the invention.

BEST MODE FOR CARRYING OUT THE INVENTION

Now, the fused aromatic ring derivative of the invention will be explained below concretely.

The fused aromatic ring derivative of the invention is a compound shown by the following formula (1):

(1)

in the formula (1), $R_a$ and $R_b$ are independently a hydrogen atom or a substituent, p is an integer of 1 to 8 and q is an integer of 1 to 11, when p or q is two or more, $R_a$s or $R_b$s may be independently the same or different, and adjacent substituents $R_a$s may form a ring, $L_1$ is a single bond or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that when the triphenylene group bonds to the 9th or 10th position of the anthracene skeleton, $L_1$ is a single bond and at least one of $R_a$s is not a hydrogen atom, $Ar_1$ is not a triphenylenyl group, and provided that substituents of $L_1$ and $Ar_1$, and $R_a$ and $R_b$ contain no amino group.

The fused aromatic derivative of the invention is preferably a compound shown by the following formula (1):

(1)

in the formula (1), $R_a$ and $R_b$ are independently a hydrogen atom or a substituent, p is an integer of 1 to 8 and q is an integer of 1 to 11, and when p or q is two or more, $R_a$s or $R_b$s may be independently the same or different and further adjacent substituents $R_a$s may form a ring, $L_1$ is a single bond or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that when $L_1$ is a single bond and at least one of $R_a$s is not a hydrogen atom, $Ar_1$ is not a triphenylenyl group, and provided that substituents of $L_1$ and $Ar_1$, and $R_a$ and $R_b$ contain no amino group.

In the formula (1), $L_1$ can bond to any position of 10 bonding positions which the anthracene ring has and to any position of 12 bonding positions which the triphenylene ring has.

In the same manner, $R_a$, $R_b$ and $Ar_1$ can bond to any position other than the bonding positions of L1.

Examples of the substituent shown by $R_a$ and $R_b$ include an alkyl group (one having preferably 1 to 20, more preferably 1 to 12 and particularly preferably 1 to 8 carbon atoms, the specific examples of which include methyl, ethyl, isopropyl, t-butyl, n-octyl, n-decyl, n-hexadecyl, cyclopropyl, cyclopentyl and cyclohexyl), an alkenyl group (one having preferably 2 to 20, more preferably 2 to 12 and particularly preferably 2 to 8 carbon atoms, the specific examples of which include vinyl, allyl, 2-butenyl and 3-pentenyl), an alkynyl group (one having preferably 2 to 20, more preferably 2 to 12 and particularly preferably 2 to 8 carbon atoms, the specific examples of which include propynyl and 3-pentynyl), a substituted or unsubstituted aryl group (one having preferably 6 to 60, more preferably 6 to 30 and particularly preferably 6 to 14 carbon atoms, the specific examples of which include phenyl, naphthyl, anthryl, and phenanthryl, examples of substituents of which include an aryl group (one having preferably 6 to 20 and particularly preferably 6 to 14 carbon atoms, the specific examples of which include phenyl, naphtyl and phenanthryl) and a heterocyclic group (one having preferably 1 to 30 and more preferably 1 to 12 carbon atoms, for example, imidazolyl, pyridyl, quinolyl, furyl, thienyl, piperidyl, morpholino, benzoxazolyl, benzimidazolyl, benzothiazolyl, carbazolyl, benzofuranyl, dibenzofuranyl, benzothiophenyl and dibenzothiophenyl)), an aryloxy group (one having preferably 6 to 20, more preferably 6 to 16 and particularly preferably 6 to 12 carbon atoms, the specific examples of which include phenyloxy and 2-naphthyloxy), an acyl group (one having preferably 1 to 20, more preferably 1 to 16 and particularly preferably 1 to 12 carbon atoms, the specific examples of which include acetyl, benzoyl, formyl and pivaloyl), an alkoxycarbonyl group (one having preferably 2 to 20, more preferably 2 to 16 and particularly preferably 2 to 12 carbon atoms, the specific examples of which include methoxycarbonyl and ethoxycarbonyl), an aryloxycarbonyl group (one having preferably 7 to 20, more preferably 7 to 16 and particularly preferably 7 to 10 carbon atoms, the specific examples of which include phenyloxycarbonyl), an acyloxy group (one having preferably 2 to 20, more preferably 2 to 16 and particularly preferably 2 to 10 carbon atoms, the specific examples of which include acetoxy and benzoyloxy), an acylamino group (one having preferably 2 to 20, more preferably 2 to 16 and particularly preferably 2 to 10 carbon atoms, the specific examples of which include acetylamino and benzoylamino), an alkoxycarbonylamino group (one having preferably 2 to 20, more preferably 2 to 16 and particularly preferably 2 to 12 carbon atoms, the specific examples of which include methoxycarbonylamino), an aryloxycarbonylamino group (one having preferably 7 to 20, more preferably 7 to 16 and particularly preferably 7 to 12 carbon atoms, the specific examples of which include phenyloxycarbonylamino), a substituted or unsubstituted sulfonylamino group (one having preferably 1 to 20, more preferably 1 to 16 and particularly preferably 1 to 12 carbon atoms, the specific examples of which include methanesulfonylamino and benzenesulfonylamino), a substituted or unsubstituted sulfamoyl group (one having preferably 0 to 20, more preferably 0 to 16 and particularly preferably 0 to 12 carbon atoms, the specific examples of which include sulfamoyl, methylsulfamoyl, dimethylsulfamoyl and phenylsulfamoyl), a substituted or unsubstituted carbamoyl group (one having preferably 1 to 20, more preferably 1 to 16 and particularly preferably 1 to 12 carbon atoms, the specific examples of which include carbamoyl, methylcarbamoyl, diethylcarbamoyl and phenylcarbamoyl), an alkylthio group (one having preferably 1 to 20, more preferably 1 to 16 and particularly preferably 1 to 12 carbon atoms, the specific examples of which include methylthio and ethylthio), an arylthio group (one having preferably 6 to 20, more preferably 6 to 16 and particularly preferably 6 to 12 carbon atoms, the specific examples of which include phenylthio), a substituted or unsubstituted sulfonyl group (one having preferably 1 to 20, more preferably 1 to 16 and particularly preferably 1 to 12 carbon atoms, the specific examples of which include mesyl and tosyl), a substituted or unsubstituted sulfinyl group (one having preferably 1 to 20, more preferably 1 to 16 and particularly preferably 1 to 12 carbon atoms, the specific examples of which include methanesulfinyl and benezenesulfinyl), a substituted or unsubstituted ureido group (one having preferably 1 to 20, more preferably 1 to 16 and particularly preferably 1 to 12 carbon atoms, the specific examples of which include ureido, methylureido and phenylureido), a substituted or unsubstituted phosphoric amide group (one having preferably 1 to 20, more preferably 1 to 16 and particularly preferably 1 to 12 carbon atoms, the specific examples of which include diethylphosphoric amide and phenylphosphoric amide), a hydroxyl group, a mercapto group, a halogen atom (for example, a fluorine atom, a chlorine atom, a bromine atom and an iodine atom), a cyano group, a sulfo group, a carboxy group, a nitro group, a hydroxamic acid group, a sulfino group, a hydrazino group, an imino group, a heterocyclic group (one having preferably 1 to 30 and more preferably 1 to 12 carbon atoms and containing, as the hetero atom, a nitrogen atom, an oxygen atom and a sulfur atom, for example, the specific examples of which include imidazolyl, pyridyl, quinolyl, furyl, thienyl, piperidyl, morpholino, benzoxazolyl, benzimidazolyl, benzothiazolyl, carbazolyl, benzofuranyl, dibenzofuranyl, benzothiophenyl and dibenzothiophenyl), and a silyl group (one having preferably 3 to 40, more preferably 3 to 30 and particularly preferably 3 to 24 carbon atoms, the examples of which include trimethylsilyl and triphenylsilyl). These substituents may be further substituted.

Among the above groups, an alkyl group, an alkenyl group, an aryl group, a carbazolyl group, a dibenzofuranyl group, a dibenzothiopheynl group, a carbazolylaryl group, a dibenzofuranylaryl group and a dibenzothiophenylaryl group are preferable.

Examples of the substituted or unsubstituted divalent linking group indicated by $L_1$ include a substituted or unsubstituted arylene having 6 to 50 ring carbon atoms. Specifically, divalent groups can be mentioned which correspond to groups obtained by eliminating one hydrogen atom from the following aryl groups:
a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4''-t-butyl-p-terphenyl-4-yl group.

Among the above groups, a substituted or unsubstituted phenylene group, particularly a phenylene group is preferable.

$L_1$ may be a divalent group formed by combination of two or more of the above-mentioned arylene groups or single bonds.

As examples of the substituted or unsubstituted aryl group having 6 to 50 ring carbon atoms indicated by $Ar_1$, a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group and the like can be given.

$Ar_1$ may be an aryl group having 6 to 50 ring carbon atoms which is substituted by a substituted or unsubstituted aryl group having 6 to 50 ring carbon atoms or a substituted or unsubstituted heteroaryl group having 5 to 50 ring atoms as mentioned below.

Examples of those groups include aryl-substituted phenyl groups such as a naphthyl-substituted phenyl group and a phenanthryl-substituted phenyl group, aryl-substituted naphthyl groups such as a phenyl-substituted naphthyl group and a binaphthyl group, and a dibenzofuranyl-substituted phenyl group.

Of these, an aryl-substituted phenyl group shown by the following formula is preferable.

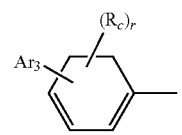

wherein $R_c$ is a hydrogen atom or a substituent, r is an integer of 1 to 4, and when r is two or more, $R_c$s may be the same or different, and $Ar_3$ is a substituted or unsubstituted aryl group having 6 to 50 ring carbon atoms.

Examples of a substituted or unsubstituted aryl group having 6 to 50 ring carbon atoms which is indicated by $Ar_3$ are the same as the examples for $Ar_1$ in the above-mentioned formula (1). Examples of substituents which is indicated by $R_c$ are the same as the examples for $R_a$ in the above-mentioned formula (1).

Examples of the substituted or unsubstituted heteroaryl group having 5 to 50 ring atoms indicated by $Ar_1$ include a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 1-dibenzofuranyl group, 2-dibenzofuranyl group, 3-dibenzofuranyl group, 4-dibenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

p is an integer of 1 to 8 and q is an integer of 1 to 11. When p is two or more, plural $R_a$s may be the same or different. In the same manner, when q is two or more, $R_b$s may be the same or different.

Adjacent $R_a$s may form a saturated or unsaturated ring.

In the formula (1), a compound where $L_1$ is a single bond, at least one of $R_a$s is not a hydrogen atom and $Ar_1$ is a triphenylenyl group is not included in the fused aromatic derivative of the invention. Substituents of $L_1$ and $Ar_1$, and $R_a$ and $R_b$ contain no amino group.

The fused aromatic derivative of the invention is preferably a compound shown by the following formula (2):

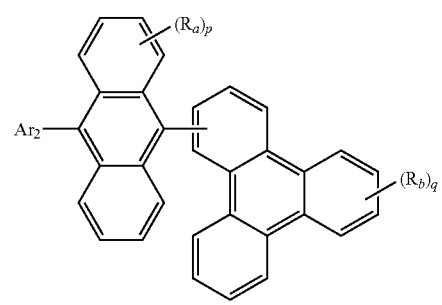

in the formula (2), $R_a$, $R_b$, p and q are the same as in the formula (1), and $Ar_2$ is a substituted or unsubstituted aryl group having 6 to 50 ring carbon atoms, provided that when at least one of $R_a$s is not a hydrogen atom, $Ar_2$ is not triphenylenyl.

Examples of the substituted or unsubstituted aryl group having 6 to 50 ring carbon atoms which is indicated by $Ar_2$ are the same as the examples of $Ar_1$ in the above-mentioned formula (1).

In the formula (2), a compound where $Ar_2$ is a substituted or unsubstituted fused aromatic ring having 10 to 20 ring carbon atoms is particularly preferable. Specific examples thereof include a 1-naphthyl group, a 2-naphthyl group, a 9-anthracenyl group, a 2-phenanthryl group and a 3-phenanthryl group.

Alternatively, a compound shown by the following formula (3) is preferable.

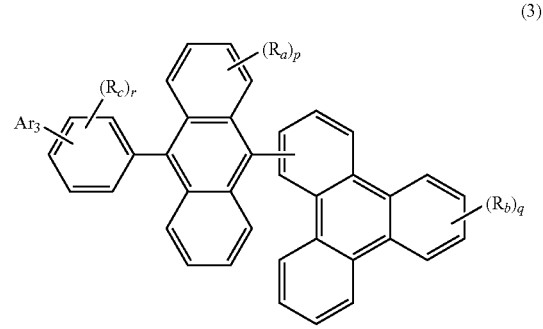

In the formula (3), $R_a$, $R_b$, p and q are the same as in the above formula (1), $R_c$ is a hydrogen atom or a substituent, r is an integer of 1 to 4, and when r is two or more, $R_c$s may be the same or different, and $Ar_3$ is a substituted or unsubstituted aryl group having 6 to 50 ring carbon atoms or a substituted or unsubstituted heteroaryl group having 5 to 50 ring atoms.

Examples of the substituted or unsubstituted aryl group having 6 to 50 ring carbon atoms and the substituted or unsubstituted heteroaryl group having 5 to 50 ring atoms which is indicated by $Ar_3$ are the same as the examples of $Ar_1$ in the above-mentioned formula (1). Examples of the substituent indicated by $R_c$ are the same as the examples of $R_a$ in the above-mentioned formula (1).

Also, in the formula (3), a compound where $Ar_3$ is a substituted or unsubstituted fused aromatic ring having 10 to 20 ring carbon atoms is particularly preferable. Specific examples thereof are the same as in the formula (2).

Alternatively, a compound shown by the following formula (4) is preferable.

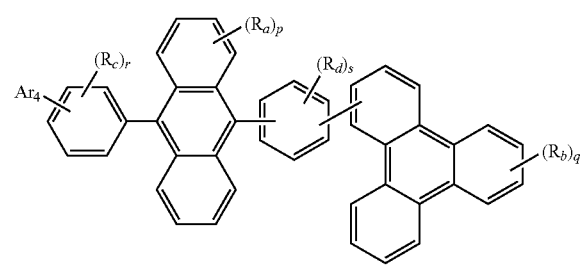

(4)

In the formula (4), $R_a$, $R_b$, p and q are the same as in the above formula (1), $R_c$ and $R_d$ are independently a hydrogen atom or a substituent, r and s are independently an integer of 1 to 4, and when r or s is two or more, $R_c$s or $R_d$s may be independently the same or different, and $Ar_4$ is a substituted or unsubstituted aryl group having 6 to 50 ring carbon atoms or a substituted or unsubstituted heteroaryl group having 5 to 50 ring atoms.

Examples of the substituted or unsubstituted aryl group having 6 to 50 ring carbon atoms and the substituted or unsubstituted heteroaryl group having 5 to 50 ring atoms which is indicated by $Ar_4$ are the same as the examples of $Ar_1$ in the above-mentioned formula (1). Examples of the substituents which are indicated by $R_c$ and $R_d$ are the same as the examples of $R_a$ in the above-mentioned formula (1).

Also, in the formula (4), a compound where $Ar_4$ is a substituted or unsubstituted fused aromatic ring having 10 to 20 ring carbon atoms is particularly preferable. Specific examples thereof are the same as in the formula (2).

Alternatively, a compound shown by the following formula (5):

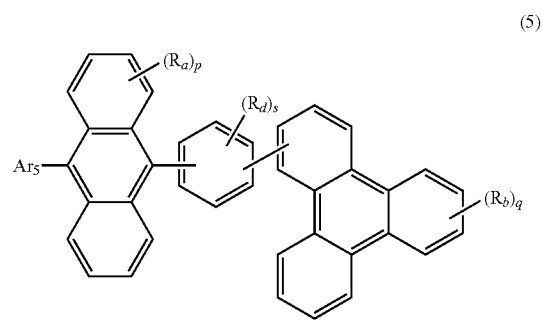

(5)

in the formula (5), $R_a$, $R_b$, p and q are the same as in the formula (1), $R_d$ is a hydrogen atom or a substituent, s an integer of 1 to 4, and when s is two or more, $R_d$s may be the same or different, and $Ar_5$ is a substituted or unsubstituted fused aromatic group having 10 to 50 ring carbon atoms.

Examples of the substituents which is indicated by $R_d$ are the same as the examples of $R_a$ in the above-mentioned formula (1).

Examples of the substituted or unsubstituted fused aromatic group having 10 to 50 ring carbon atoms which is indicated by $Ar_5$ include a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-prenyl group, a 4-pyrenyl group, a 3-methyl-2-naphthyl group, a 4-methyl-1-naphthyl group and a 4-methyl-1-anthryl group.

As $Ar_5$, a substituted or unsubstituted naphthyl group is particularly preferable. As the substituent, the same groups as $R_a$ in the formula (1) may be mentioned. Among them, a 1-naphthyl group and a 2-naphthyl group are preferable.

Examples of the fused aromatic ring derivative of the invention will be shown below:

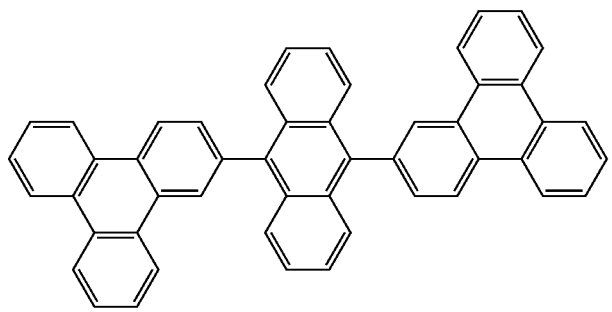

-continued
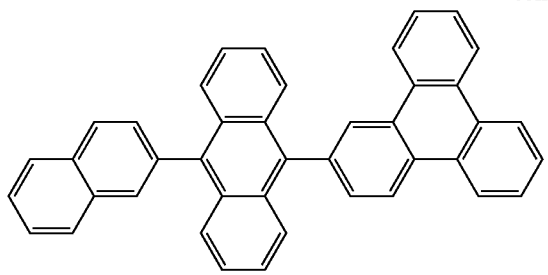
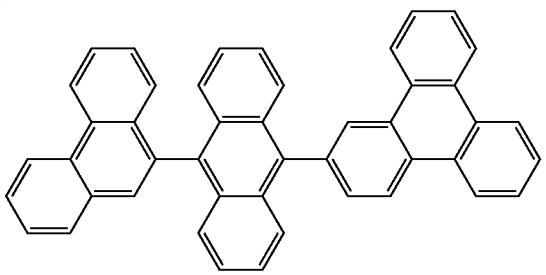
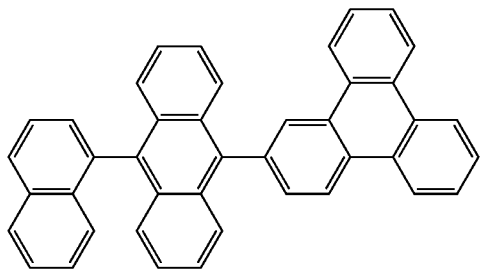
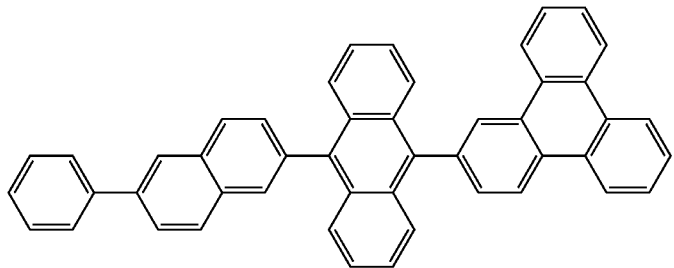
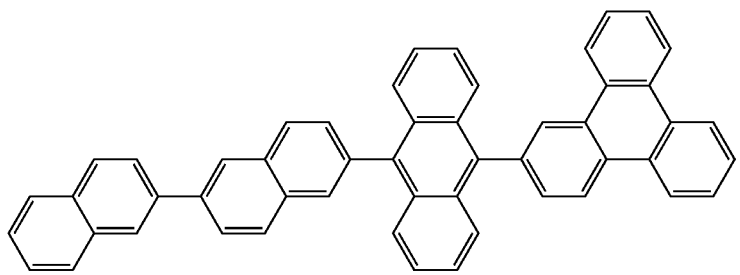
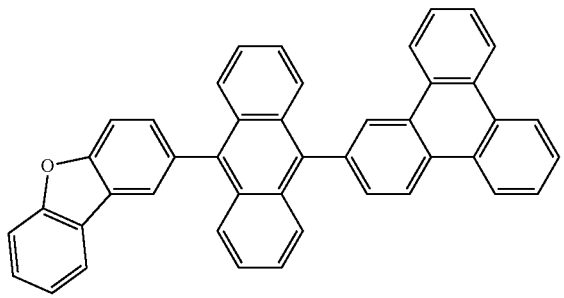
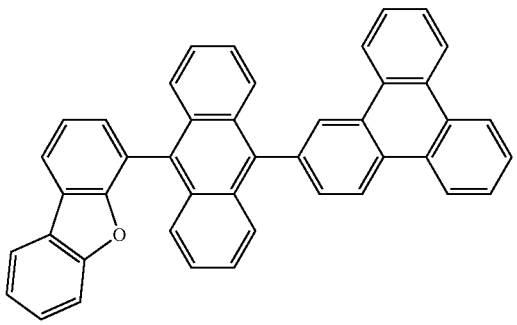
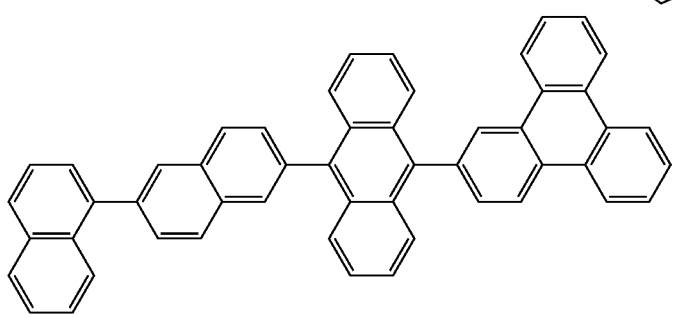

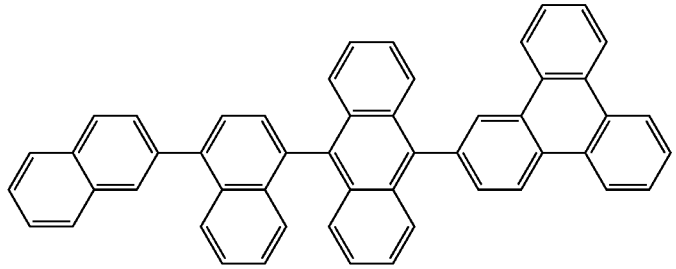
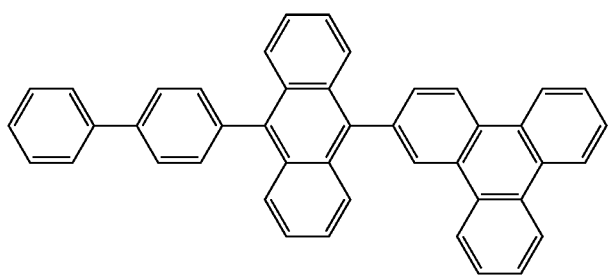
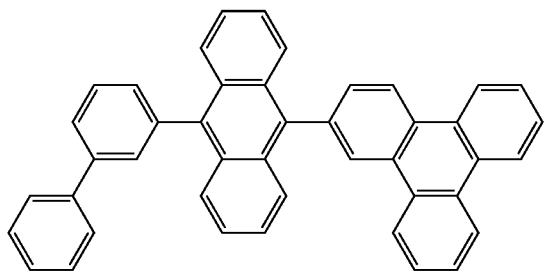
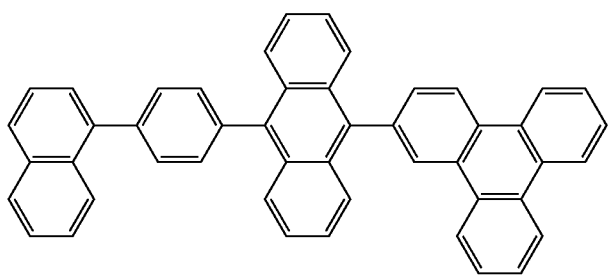
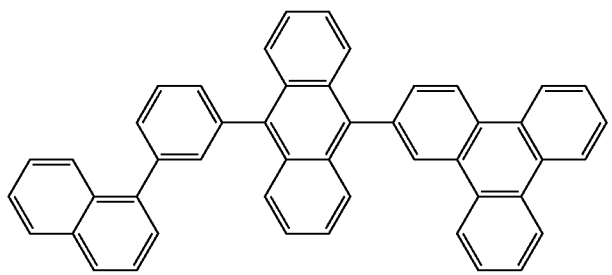
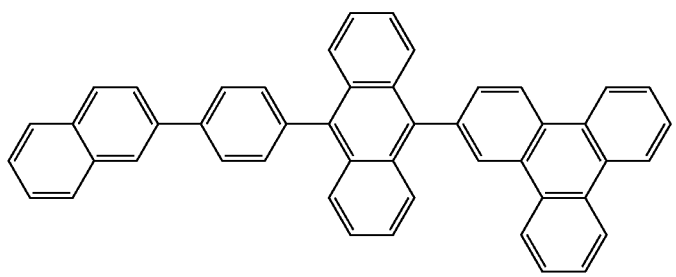

-continued
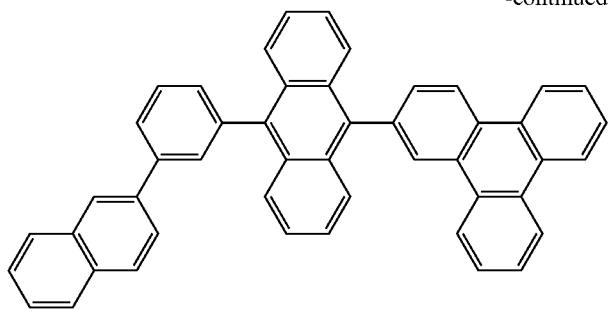
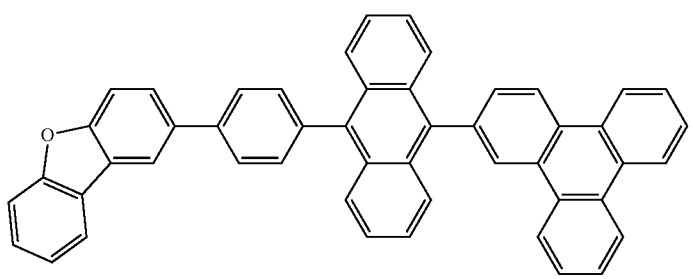
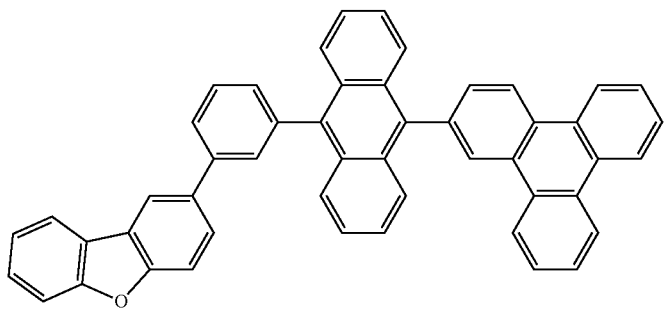
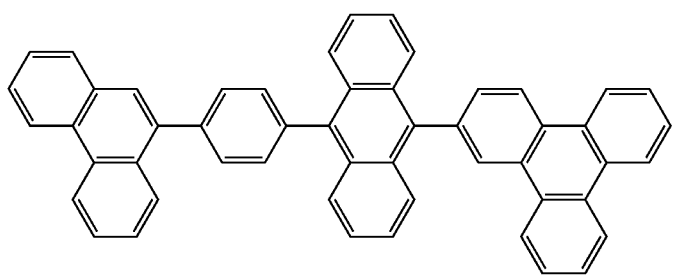
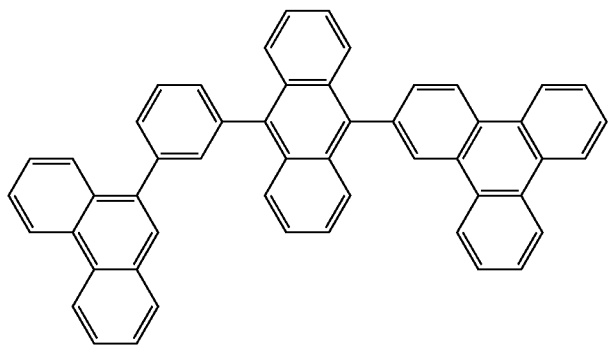

-continued
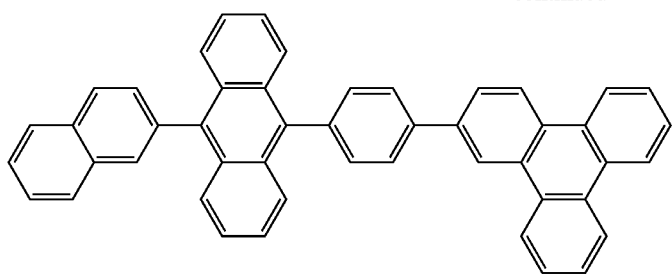
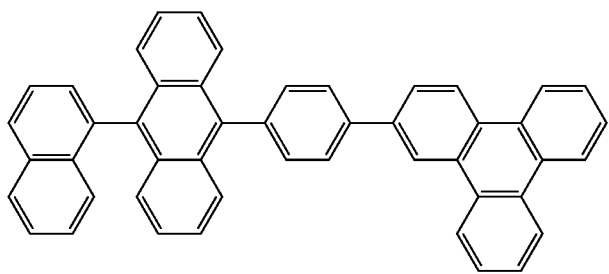
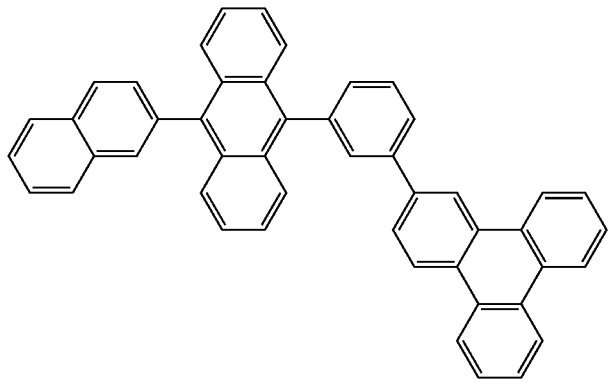
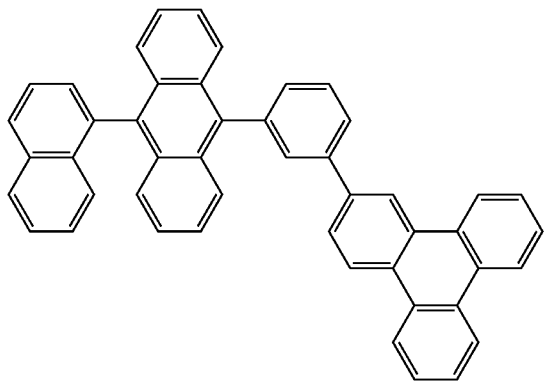
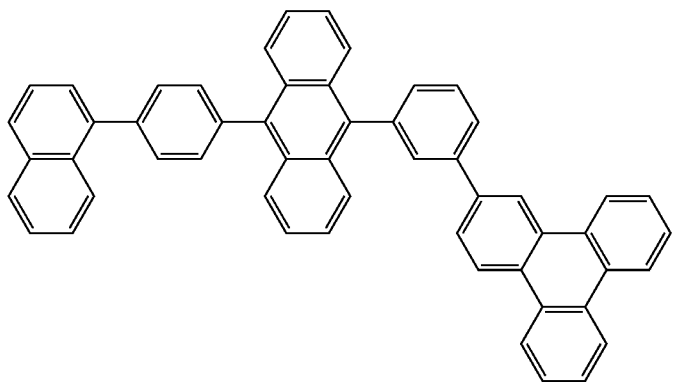

-continued
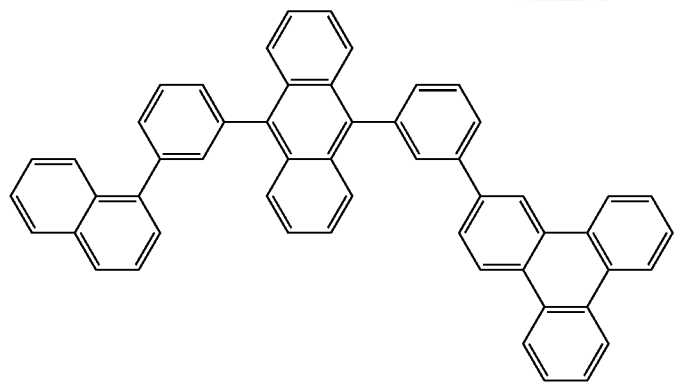
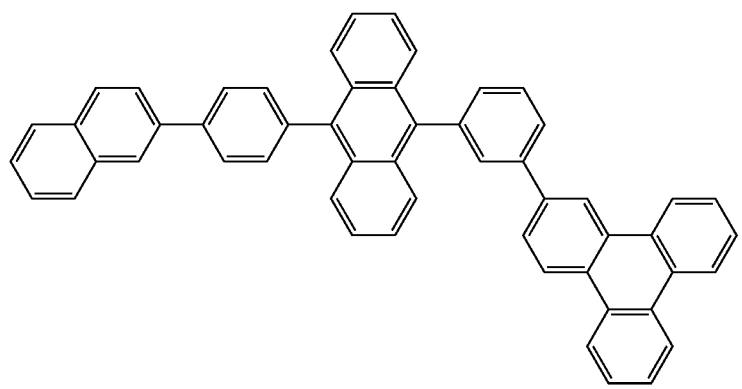
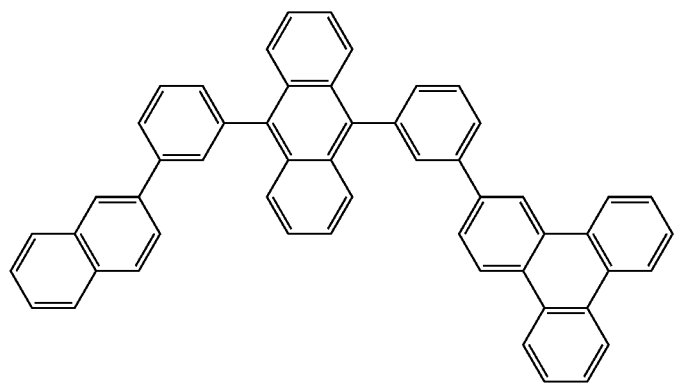
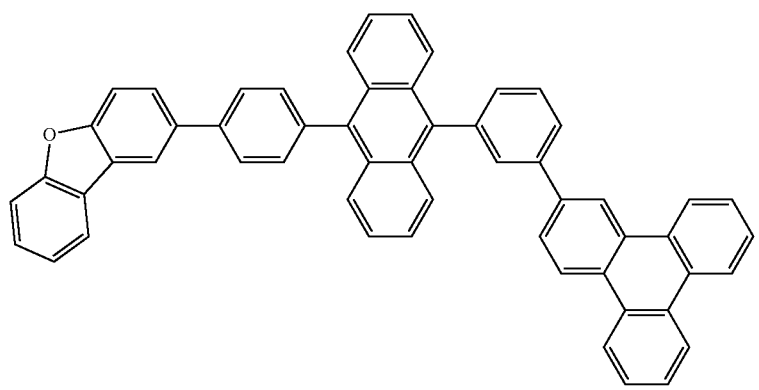

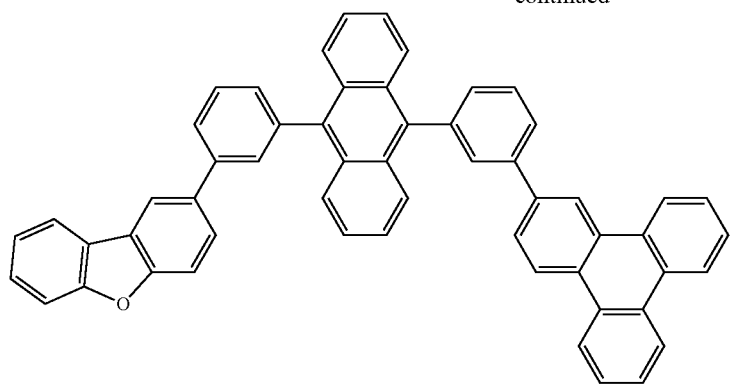
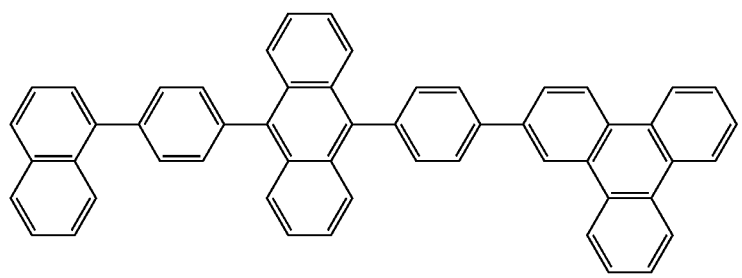
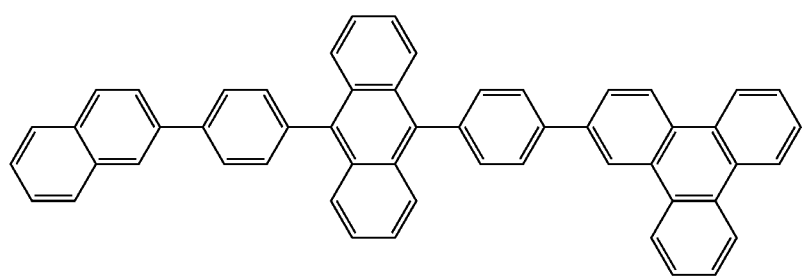
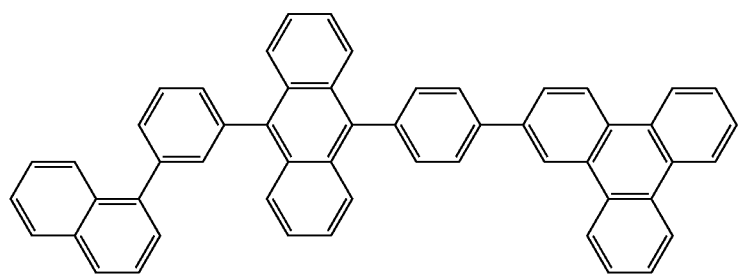
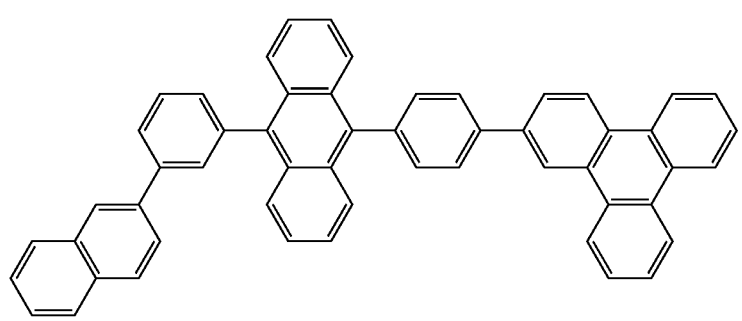

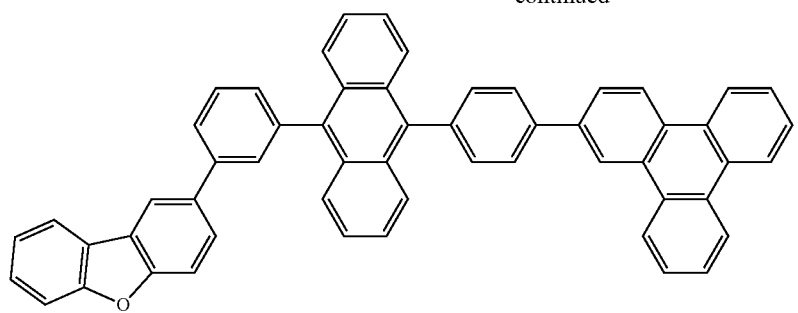
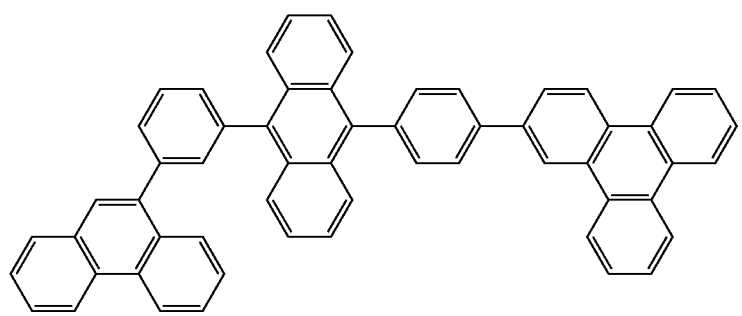
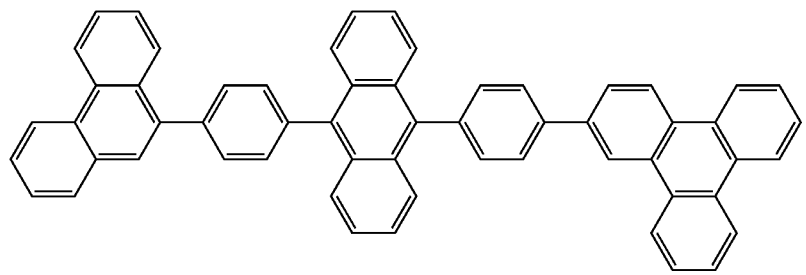
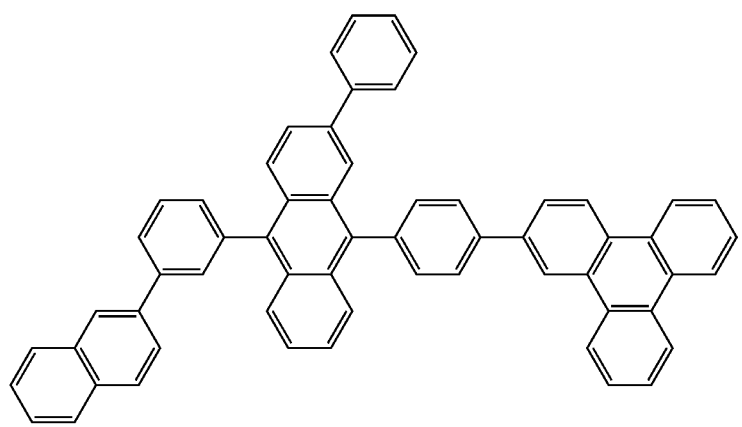

-continued
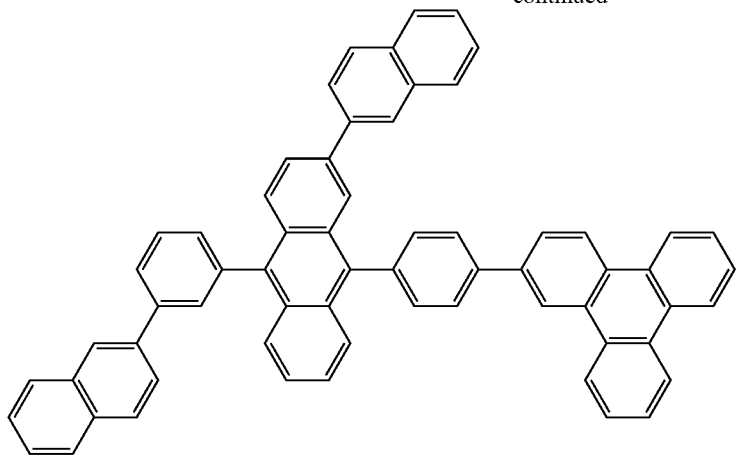
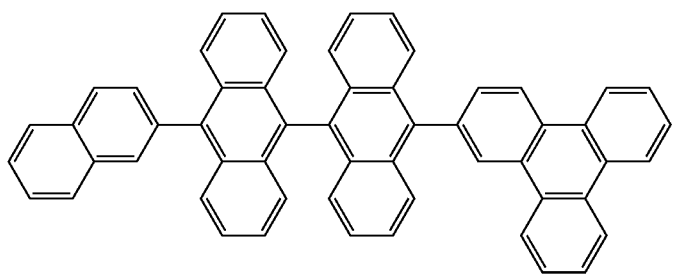
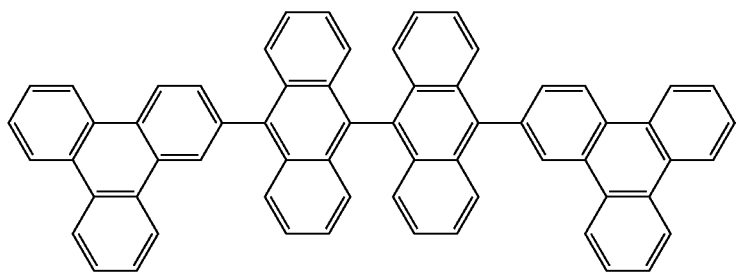
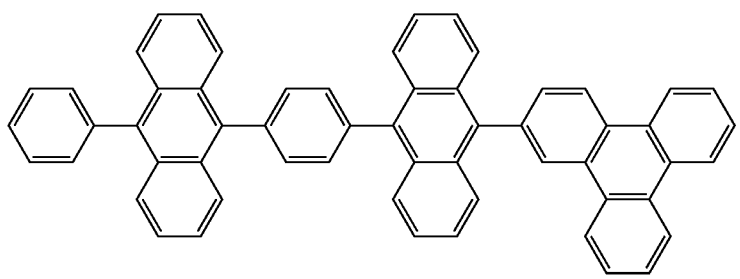
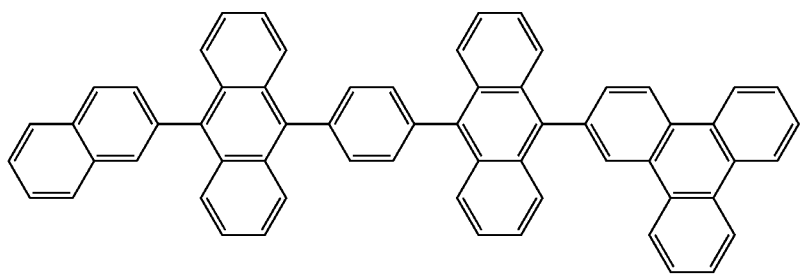

-continued
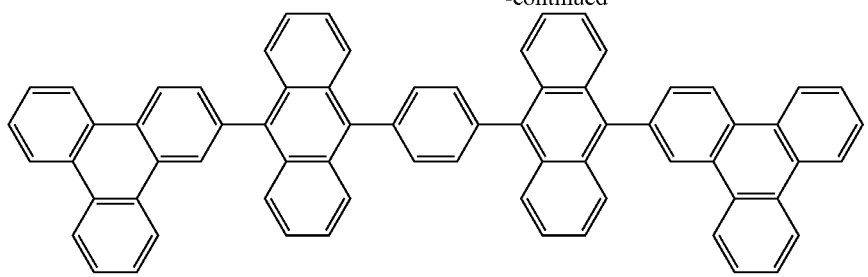
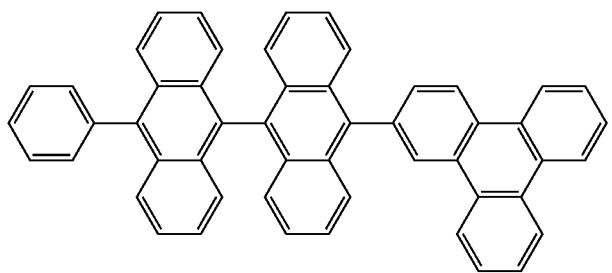
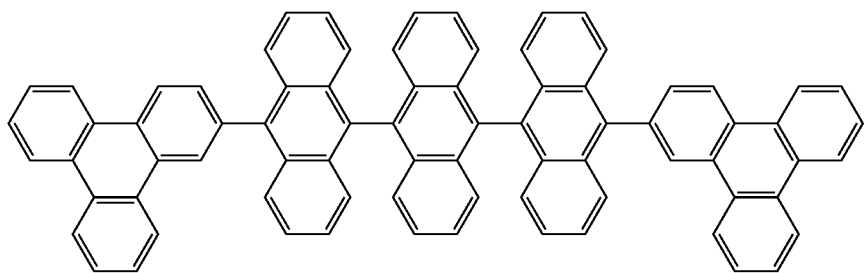
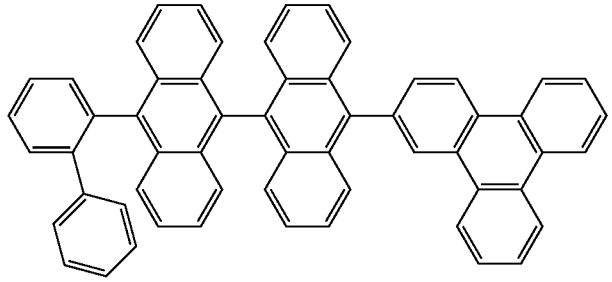
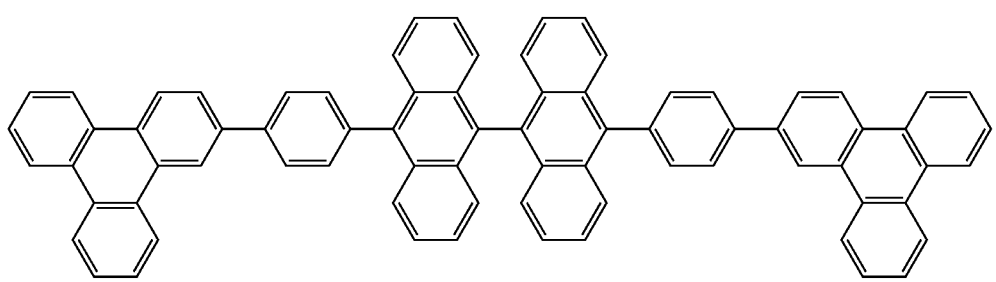
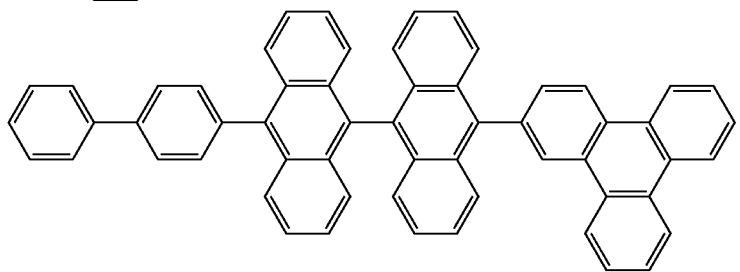

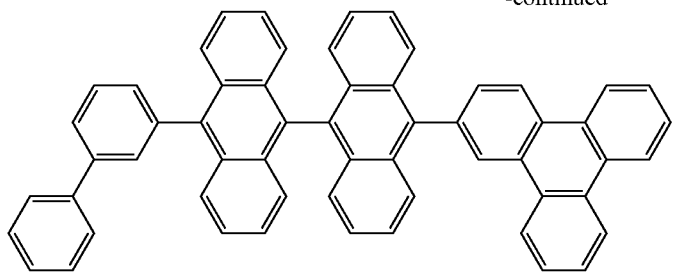
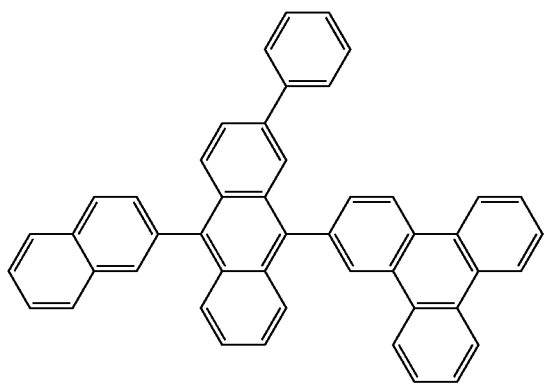
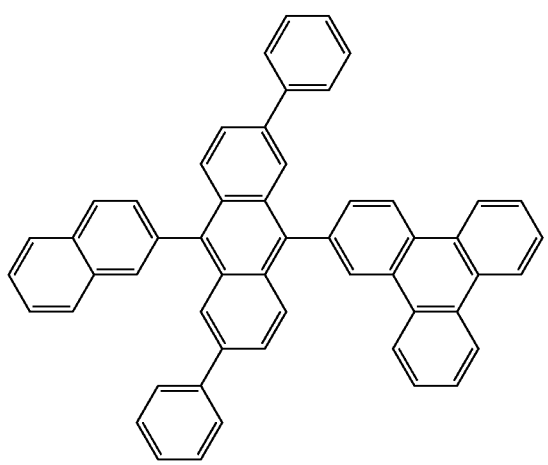
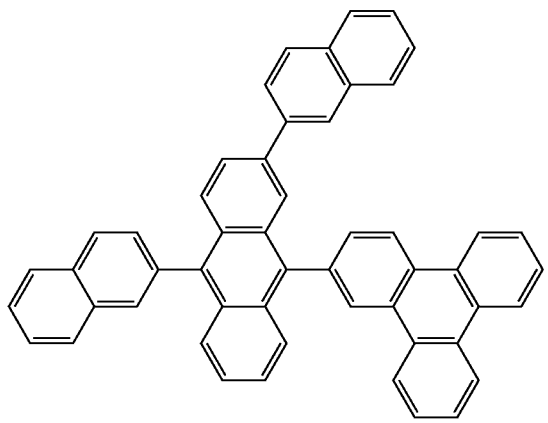
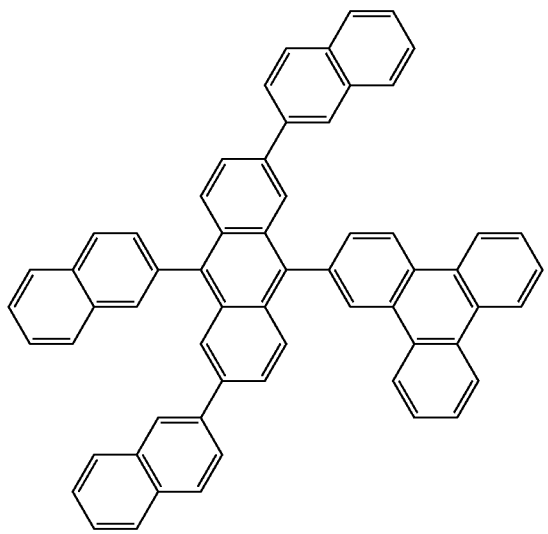

-continued
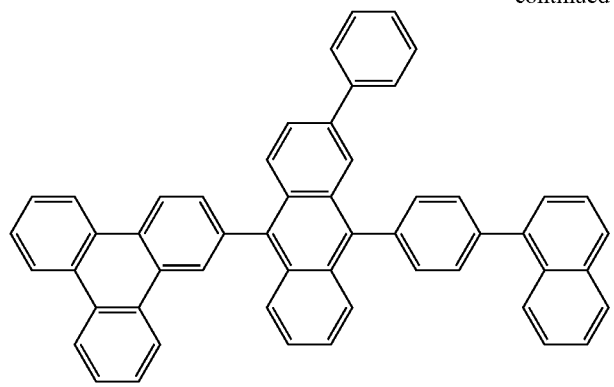
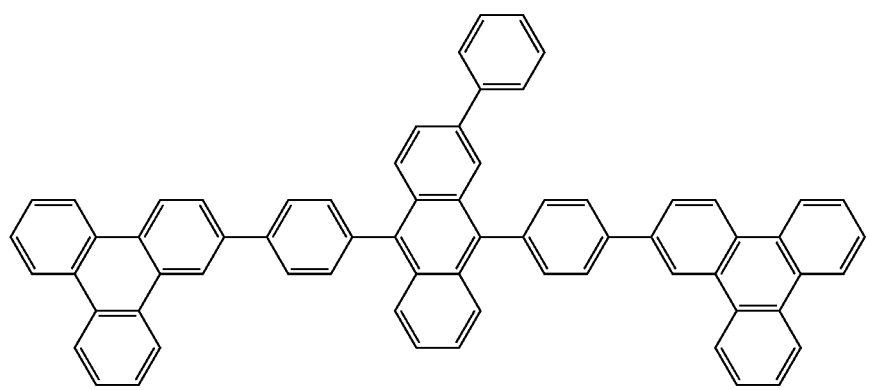
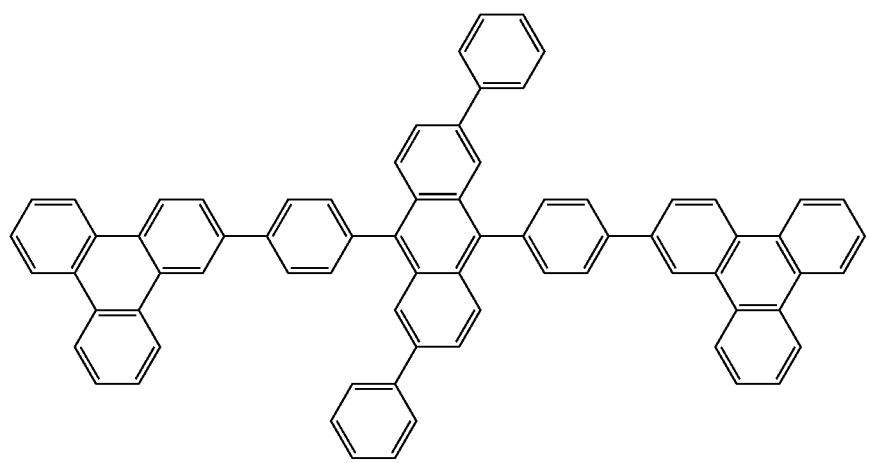
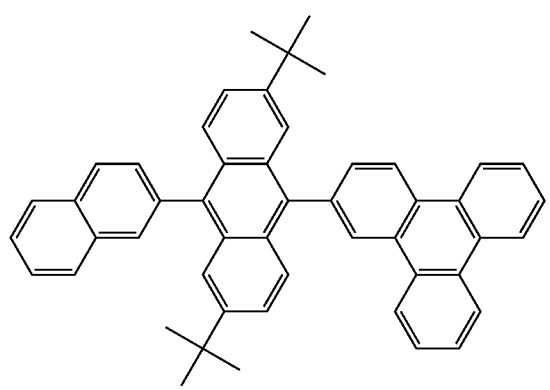 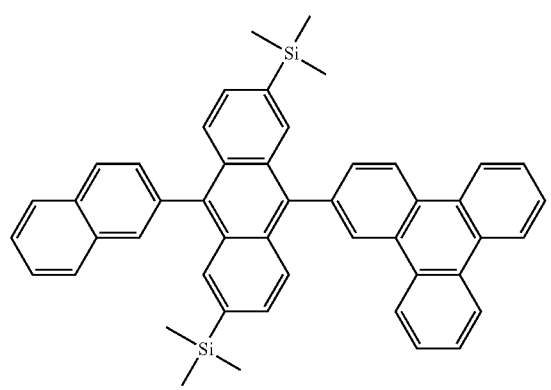

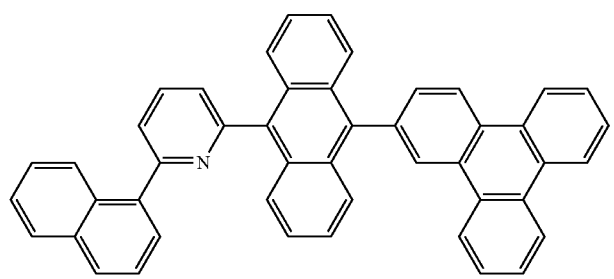
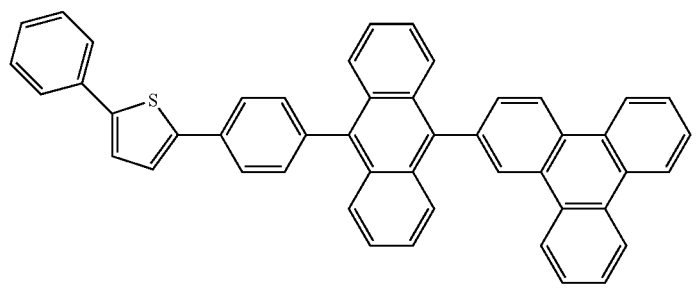
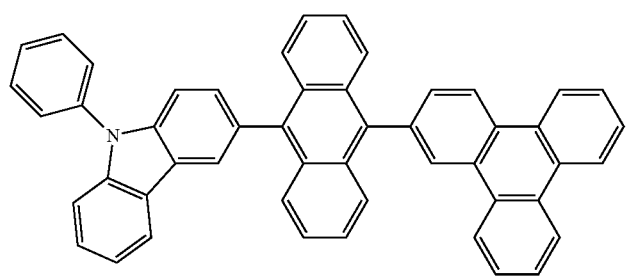
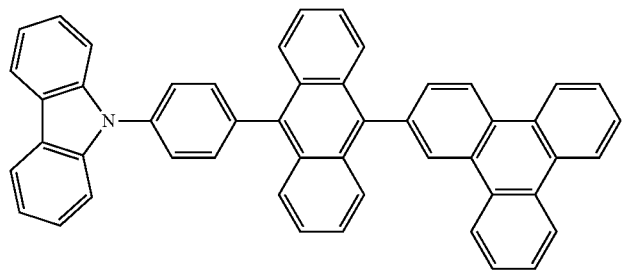
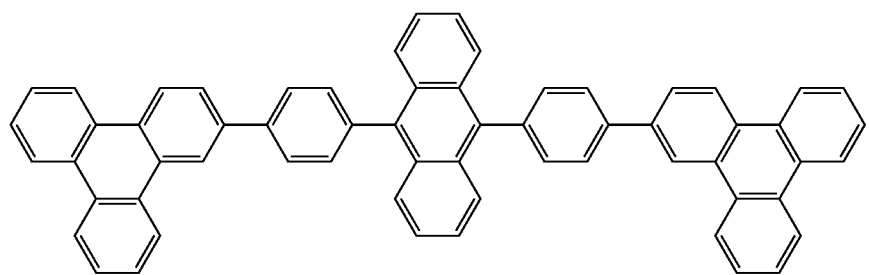

-continued
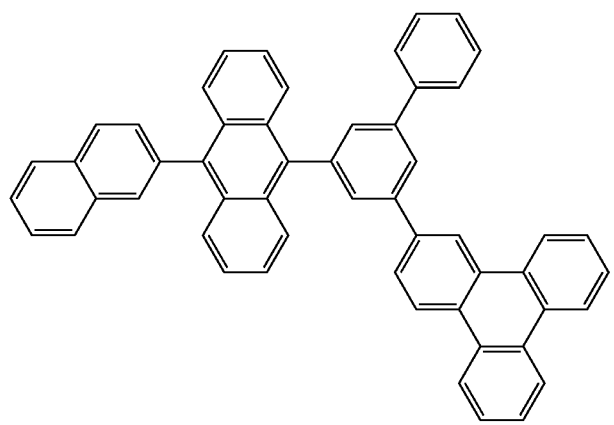
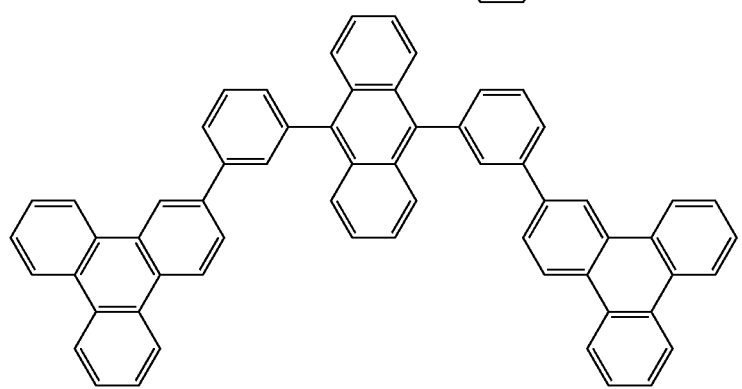
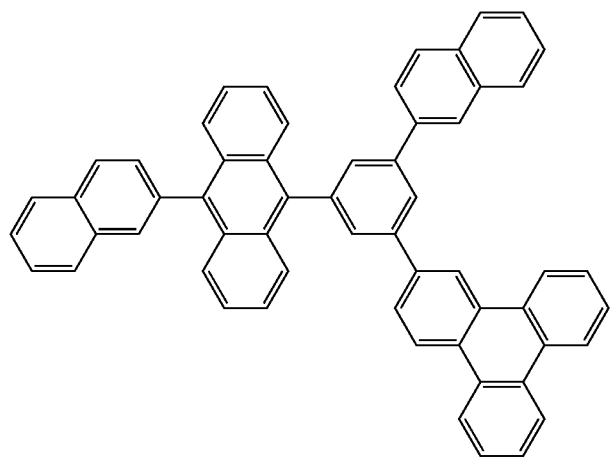
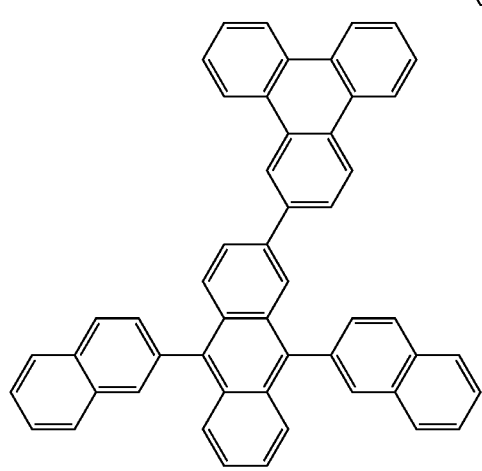
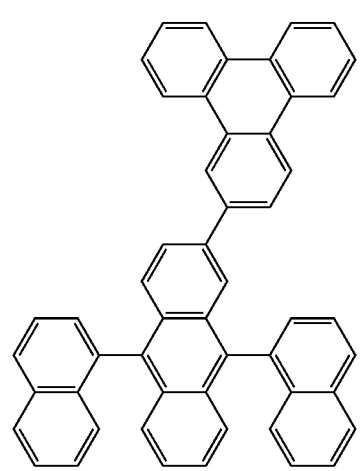

-continued
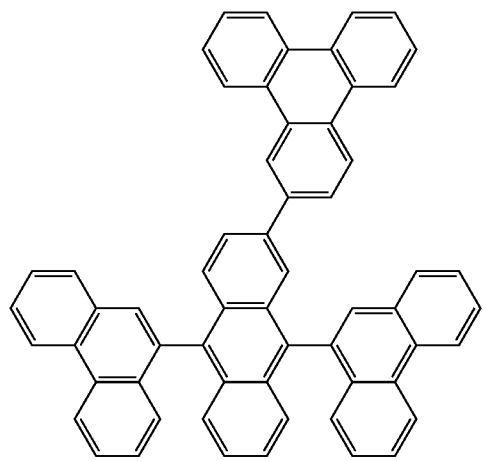
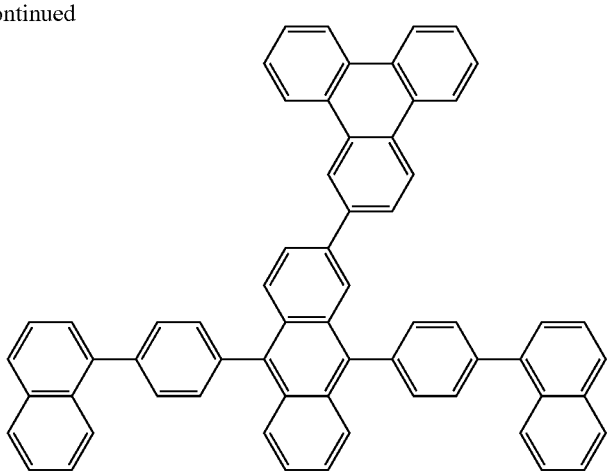
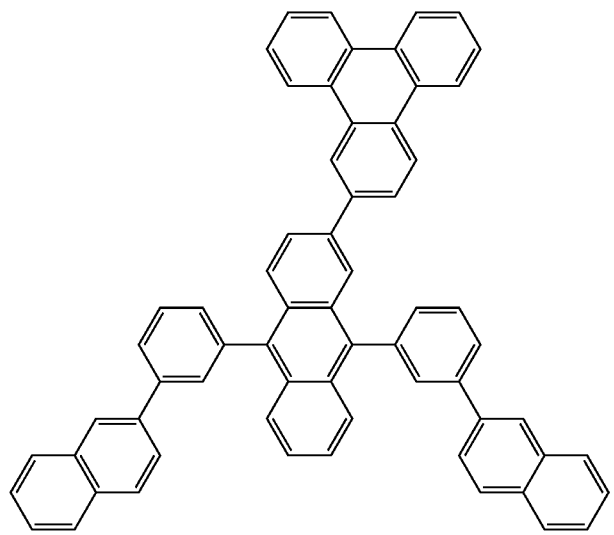
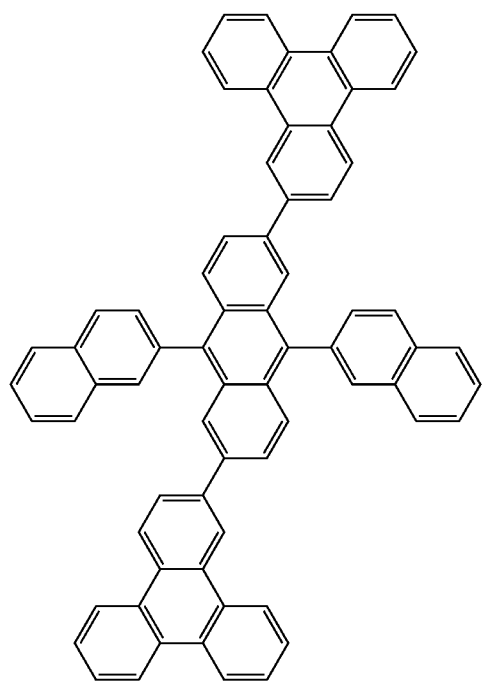
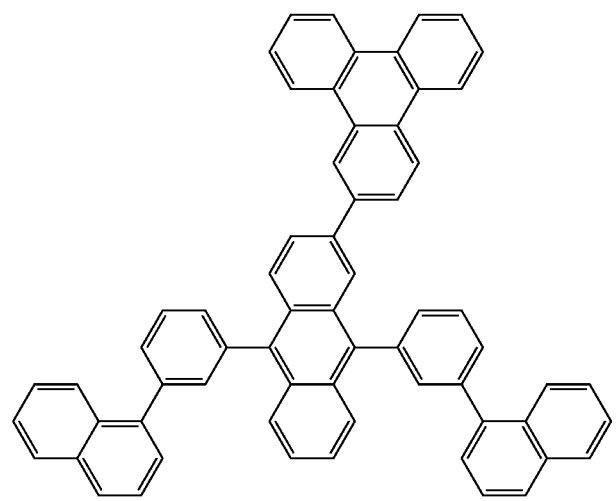

The fused aromatic derivative of the invention can be synthesized by cyclization of ortho-terphenyl derivative. The synthesis will be specifically explained in examples.

The fused aromatic derivative of the invention (hereinafter often referred to as the compound of the invention) is suitably used for a material for an organic EL device, particularly as the emitting material. The material for an organic EL device of the invention comprises the fused aromatic derivative, or consists essentially of the fused aromatic derivative of the invention.

The organic EL device of the invention comprises an anode, a cathode and one or more organic thin layers comprising an emitting layer between the anode and the cathode, and at least one of the organic thin layers comprise the above-mentioned compound of the invention.

Representative configurations of the organic EL device of the invention can be given below.

(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron-barrier layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode The representative examples of the configuration of the organic EL device of the invention are, however, not limited to the above. Of these, the configuration (8) is preferable.

The configuration (8) is shown in FIG. 1. This organic EL device comprises an anode 10, a cathode 20, and a hole-injecting layer 30, a hole-transporting layer 32, an emitting layer 34 and an electron-injecting layer 36 between the anode and the cathode. The hole-injecting layer 30, the hole-transporting layer 32, the emitting layer 34 and the electron-injecting layer 36 correspond to the plurality of organic thin film layers. At least one of these organic thin film layers 30, 32, 34 and 36 comprises the compound of the invention.

In the organic EL device of the invention, although the compound of the invention may be used in any of the above-mentioned organic thin film layers, it is preferred that the compound of the invention be used in the emitting layer. In each of the organic thin film layers, the compound of the invention may be used either singly or in mixture with other compounds. In the device of the invention, it is preferred that the emitting layer contain the compound of the invention as a host material and contain at least, one of a fluorescent dopant and a phosphorescent dopant.

In the invention, it is preferred that the emitting layer consist essentially of the compound of the invention and the above-mentioned dopant.

The content of the compound of the invention in the organic thin film layers is preferably 30 to 100 mol %.

Each member of the organic EL device will be explained below.

The organic EL device is normally formed on a substrate. The substrate supports the organic EL device. It is preferable to use a smooth substrate. If light is outcoupled through the substrate, it is preferred that the substrate be a transparent substrate with a transmission to visible rays with a wavelength of 400 to 700 nm of 50% or more.

As such transparent substrate, a glass plate, a synthetic resin plate or the like are preferably used. Examples of the glass plate include plates of soda-lime glass, barium/strontium-containing glass, lead glass, aluminosilicate glass, borosilicate glass, barium borosilicate glass, quartz, or the like. Examples of the synthetic resin plates include plates of a polycarbonate resin, an acrylic resin, a polyethylene terephthalate resin, a polyether sulfide resin, a polysulfone resin, or the like.

It is effective that the anode injects holes to the hole-injecting layer, the hole-transporting layer or the emitting layer and has a work function of 4.5 eV or more. Specific examples of the anode material include indium tin oxide (ITO), a mixture of indium oxide and zinc oxide (IZO), a mixture of ITO and cerium oxide (ITCO), a mixture of IZO and cerium oxide (IZCO), a mixture of indium oxide and cerium oxide (ICO), a mixture of zinc oxide and aluminum oxide (AZO), tin oxide (NESA), gold, silver, platinum and copper.

The anode can be formed from these electrode materials by a vapor deposition method, a sputtering method or the like.

In the case where emission from the emitting layer is outcoupled through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

The emitting layer has the following functions.
(i) Injection function: function of allowing injection of holes from the anode or hole-injecting layer and injection of electrons from the cathode or electron-injecting layer upon application of an electric field
(ii) Transporting function: function of moving injected carriers (electrons and holes) due to the force of an electric field
(iii) Emission function: function of recombining electrons and holes to emit light As the method of forming the emitting layer, a known method such as deposition, spin coating, or an LB method may be applied. It is preferable that the emitting layer be a molecular deposition film. The molecular deposition film is a film formed by deposition of a material compound in a gas phase, or by solidification of a material compound in the form of a solution or in a liquid phase. The molecular deposition film can be usually distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

In the organic EL device of the invention, it is preferred that the emitting layer contain the emitting material of the invention as a host and contain at least one of a phosphorescent dopant and a fluorescent dopant. An emitting layer containing these dopants may be stacked on an emitting layer containing the compound of the invention.

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. The phosphorescent compounds can be used individually or as a combination of two or more kinds.

As a porphyrin metal complex, a porphyrin platinum complex is preferable.

There are various ligands forming an ortho-metalated metal complex. Preferable ligands include compounds having a phenylpyridine skeleton, a bipyridyl skeleton or a phenanthroline skeleton, 2-phenylpiridine, 7,8-benzoquinoline, 2-(2-thienyl)pyridine, 2-(1-naphthyl)pyridine and 2-phenylquinoline derivatives. These ligands may have a substituent, if necessary. Ligands to which fluorides, e.g. a trifluoromethyl group, being introduced as a substituent are particularly preferable as a blue dopant. As an auxiliary ligand, preferred are ligands other than the above-mentioned ligands, such as acetylacetonate and picric acid may be contained.

Examples of such metal complexes include tris(2-phenylpiridine)iridium, tris(2-phenylpiridine)ruthenium, tris(2-phenylpiridine)palladium, bis(2-phenylpiridine)platinum, tris(2-phenylpiridine)osmium, tris(2-phenylpiridine)rhenium, octaethyl platinum porphyrin, octaphenyl platinum porphyrin, octaethyl palladium porphyrin and octaphenyl palladium porphyrin. However, not limited to the above, and an appropriate complex can be selected depending on the required emitting color, device performance and a host compound used.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

As for the fluorescent dopant, it is preferable to select a compound from amine-based compounds, aromatic compounds, chelate complexes such as tris(8-quinolilate)aluminum complexes, coumarin derivatives, tetraphenylbutadiene derivatives, bisstyrylarylene derivatives, oxadiazole derivatives or the like, taking into consideration required emission colors. Of these, styrylamine compounds, styryldiamine compounds, arylamine compounds and aryldiamine compounds are further preferable. Fused polycyclic aromatic compounds which are not an amine compound are also preferable. These fluorescent dopants may be used singly or in combination of two or more. The content of a fluorescent dopant in the emitting layer is not particularly limited and can be appropriately selected according to purposes; for example, it is 0.1 to 70 mass %, preferably 1 to 30 mass %.

As the styrylamine compound and the styryldiamine compound, those shown by the following formula (A) are preferable.

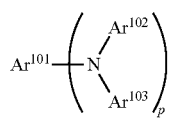

(A)

wherein $Ar^{101}$ is a group with a valence of p corresponding to a phenyl group, a naphthyl group, a biphenyl group, a terphenyl group, a stilbenzyl group or a distyrylaryl group, $Ar^{102}$ and $Ar^{103}$ are independently an aromatic hydrocarbon group having 6 to 20 carbon atoms, $Ar^{101}$, $Ar^{102}$ and $Ar^{103}$ may be substituted, one of $Ar^{101}$ to $Ar^{103}$ is substituted by a styryl group, further preferably, at least one of $Ar^{102}$ and $Ar^{103}$ is substituted by a styryl group, and p is an integer of 1 to 4, preferably an integer of 1 to 2.

Here, as the aromatic hydrocarbon group having 6 to 20 carbon atoms, a phenyl group, a naphthyl group, an anthranyl group, a phenanthryl group, a terphenyl group or the like can be given.

As the arylamine compound and the aryldiamine compound, those shown by the following formula (B) are preferable.

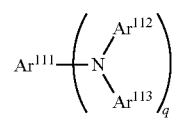

(B)

wherein $A^{111}$ is a substituted or unsubstituted aromatic group with a valence of q having 5 to 40 ring carbon atoms, $Ar^{112}$ and $Ar^{113}$ are independently a substituted or unsubstituted aryl group having 5 to 40 ring carbon atoms, and q is an integer of 1 to 4, preferably an integer of 1 to 2.

Examples of the aryl group having 5 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzanthracenyl group, a phenylanthranyl group and a bisanthracenyl group. Preferred are a naphthyl group, an anthranyl group, a chrysenyl group and a pyrenyl group.

As the $Ar^{111}$, the above-mentioned q-valent group is preferable. When $Ar^{111}$ is a divalent group, groups shown by the following formulas (C) and (D) are preferable. A group shown by the formula (D) is more preferable.

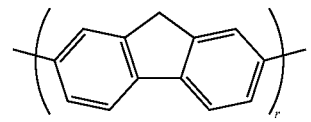

(C)

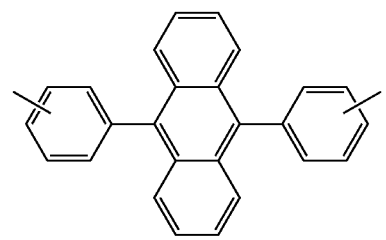

(D)

(in the formula (C), r is an integer of 1 to 3)

Preferred substituents for the above-mentioned aryl group include an alkyl group having 1 to 6 carbon atoms (ethyl, methyl, i-propyl, n-propyl, s-butyl, t-butyl, pentyl, hexyl, cyclopentyl, cyclohexyl, or the like); an alkoxy group having 1 to 6 carbon atoms (ethoxy, methoxy, i-propoxy, n-propoxy, s-buthoxy, t-buthoxy, penthoxy, hexyloxy, cyclopentoxy, cyclohexyloxy, or the like); an aryl group having 5 to 40 ring carbon atoms; an amino group substituted with an aryl group having 5 to 40 ring carbon atoms; an ester group with an aryl group having 5 to 40 ring carbon atoms; an ester group with an alkyl group having 1 to 6 carbon atoms; a cyano group; a nitro group; and a halogen atom.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

The hole-transporting layer and the hole-injecting layer are layers which help the injection of holes into the emitting layer so as to transport holes to an emitting region, and have a large hole mobility and normally have such a small ionization energy as 5.5 eV or less. As the material for the hole-injecting layer and the hole-transporting layer, a material which transports holes to the emitting layer at a lower electrical field is preferable, and the hole mobility thereof is preferably $10^{-4}$ $cm^2$/N·second or more when an electric field of, e.g., $10^4$ to $10^6$ V/cm is applied.

There are no particular restrictions on the material for the hole-injecting layer and the hole-transporting layer. The material can be arbitrarily selected from materials which have been widely used as a hole-transporting material of photoconductive materials and known materials used in a hole-injecting layer and a hole-transporting layer of organic EL devices.

In the hole-injecting layer and the hole-transporting layer, an aromatic amine derivative shown by the following formula can be used, for example.

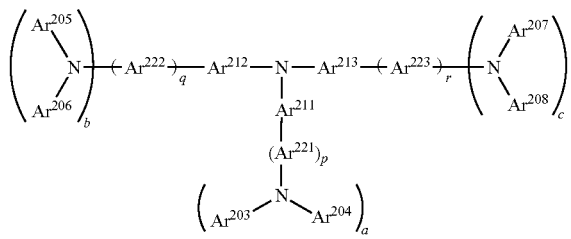

wherein $Ar^{211}$ to $Ar^{213}$ and $Ar^{221}$ to $Ar^{223}$ are independently a substituted or unsubstituted aryl group having 6 to 50 ring carbon atoms or a substituted or unsubstituted heteroaryl group having 5 to 50 ring atoms, $Ar^{203}$ to $Ar^{208}$ are independently a substituted or unsubstituted arylene group having 6 to 50 ring carbon atoms or a substituted or unsubstituted heteroarylene group having 5 to 50 ring atoms, a to c and p to r are independently an integer of 0 to 3, and $Ar^{203}$ and $Ar^{204}$, $Ar^{205}$ and $Ar^{206}$, or $Ar^{207}$ and $Ar^{208}$ may be bonded to each other to form a saturated or unsaturated ring.

Examples of the substituted or unsubstituted aryl group having 6 to 50 ring carbon atoms or the substituted or unsubstituted heteroaryl group having 5 to 50 ring atoms are the same as the examples of $Ar_1$ in the above-mentioned formula (1).

Further, the compound shown by the following formula can be used in the hole-injecting layer and the hole-transporting layer.

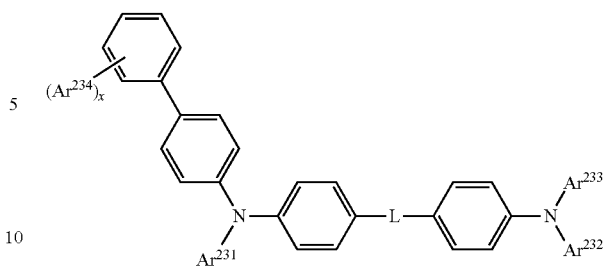

wherein $Ar^{231}$ to $Ar^{234}$ are independently a substituted or unsubstituted aryl group having 6 to 50 ring carbon atoms, or a substituted or unsubstituted heteroaryl group having 5 to 50 ring atoms, L is a linking group, which is a single bond, a substituted or unsubstituted arylene group having 6 to 50 ring carbon atoms or a substituted or unsubstituted heteroarylene group having 5 to 50 ring atoms, x is an integer of 0 to 5, and $Ar^{232}$ and $Ar^{233}$ may be bonded to each other to form a saturated or unsaturated ring.

As specific examples of the substituted or unsubstituted aryl group having 6 to 50 ring carbon atoms and substituted or unsubstituted heteroaryl group having 5 to 50 ring atoms, the same as those exemplified for $Ar_1$ in the above-mentioned formula (1) can be given.

As specific examples of the material for the hole-injecting layer and the hole-transporting layer, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalkone derivative, an oxazole derivative, a styrylanthracene derivative, a fluorenone derivative, a hydrazone derivative, a stilbene derivative, a silazane derivative, an aniline-based copolymer, and conductive high-molecular oligomers (in particular, a thiophene oligomer) can be given.

As the material for the hole-injecting layer and the hole-transporting layer, although the above-mentioned materials can be used, it is preferable to use a porphyrin compound, an aromatic tertiary amine compound and a styrylamine compound. It is particularly preferable to use an aromatic tertiary amine compound.

It is preferable to use a compound having two fused aromatic rings in the molecule thereof, for example, 4,4'-bis(N-(1-naphthyl)-N-phenylamino)biphenyl (abbreviated by NPD, hereinafter), and 4,4',4''-tris(N-(3-methylphenyl)-N-phenylamino)triphenylamine (abbreviated by MTDATA, hereinafter) wherein three triphenylamine units are linked in a star-burst form.

In addition to the above, a nitrogen-containing heterocyclic derivative shown by the following formula can also be used.

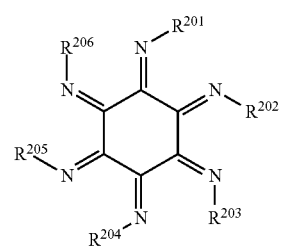

wherein $R^{201}$ to $R^{206}$ are independently a substituted or unsubstituted alkyl group, a substituted or unsubstituted aryl group, a substituted or unsubstituted aralkyl group, a substituted or unsubstituted heterocyclic group, and $R^{201}$ and $R^{202}$, $R^{203}$ and $R^{204}$, $R^{205}$ and $R^{206}$, $R^{201}$ and $R^{206}$, $R^{202}$ and $R^{203}$, or $R^{204}$ and $R^{205}$ may form a fused ring.

Further, the following compound can also be used.

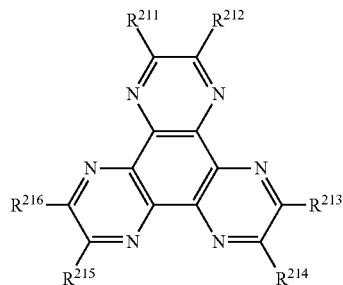

wherein $R^{211}$ to $R^{216}$ are substituents; preferably they are independently an electron-attracting group such as a cyano group, a nitro group, a sulfonyl group, a carbonyl group, a trifluoromethyl group and a halogen.

Further, an inorganic compound such as p-type Si and p-type SiC can also be used as a material for the hole-injecting layer and the hole-transporting layer.

The hole-injecting layer and the hole-transporting layer can be formed from the above-mentioned compounds by a known method such as vapor vacuum deposition, spin coating, casting or LB technique. The film thickness of the hole-injecting layer and the hole-transporting layer is not particularly limited, and is usually from 5 nm to 5 μm. The hole-injecting layer and the hole-transporting layer may be a single layer made of one or two or more of the above-mentioned materials, or may be of, a structure in which hole-injecting layers and hole-transporting layers made of different compounds are stacked.

The organic semiconductor layer is a layer for helping the injection of holes or electrons into the emitting layer, and is preferably a layer having an electric conductivity of $10^{-10}$ S/cm or more. As the material of such an organic semiconductor layer, electroconductive oligomers such as thiophene-containing oligomers or arylamine-containing oligomers and electroconductive dendrimers such as arylamine-containing dendrimers may be used.

The electron-injecting layer and the electron-transporting layer are layers which assist injection of electrons into the emitting layer and transport electrons to the emitting region, and exhibit a high electron mobility. The adhesion-improving layer is a kind of the electron-injecting layer which is made of a material exhibiting particularly good adhesion to the cathode.

The thickness of the electron-transporting layer is arbitrarily selected in the range of 5 nm to 5 μm. When the electron-transporting layer has a thick thickness, it is preferable that the electron mobility be $10^{-5}$ cm$^2$/Vs or more at an applied electric field of $10^4$ to $10^6$ V/cm in order to prevent an increase in voltage.

The material used in the electron-injecting layer and the electron-transporting layer is preferably a metal complex of 8-hydroxyquinoline or a derivative thereof, or an oxadiazole derivative. Specific examples of the metal complex of 8-hydroxyquinoline or derivative thereof include metal chelate oxynoid compounds containing a chelate of oxine (generally, 8-quinolinol or 8-hydroxyquinoline), e.g. tris(8-quinolinolato)aluminum.

As examples of the oxadiazole derivative, an electron-transporting compound shown by the following formula can be given.

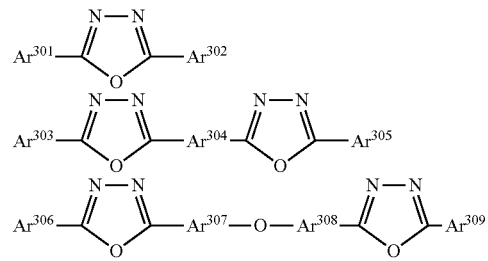

wherein $Ar^{301}$, $Ar^{302}$, $Ar^{303}$, $Ar^{305}$, $Ar^{306}$ and $Ar^{309}$ are independently a substituted or unsubstituted aryl group, and $Ar^{304}$, $Ar^{307}$ and $Ar^{308}$ are independently a substituted or unsubstituted arylene group.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

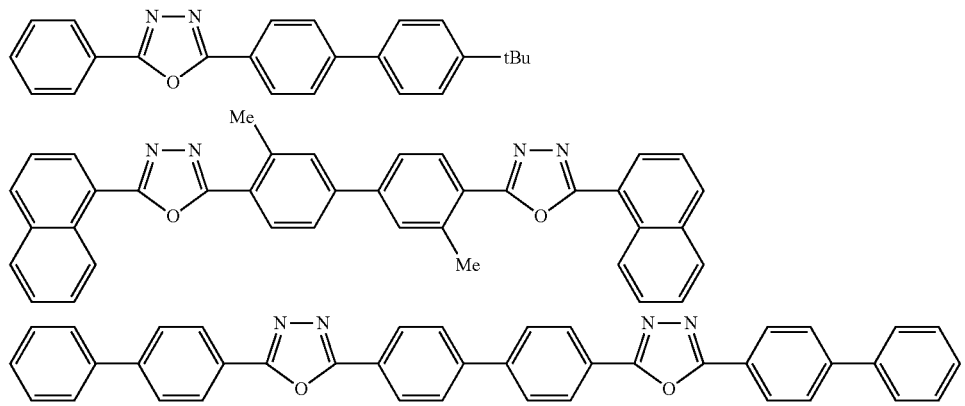

-continued

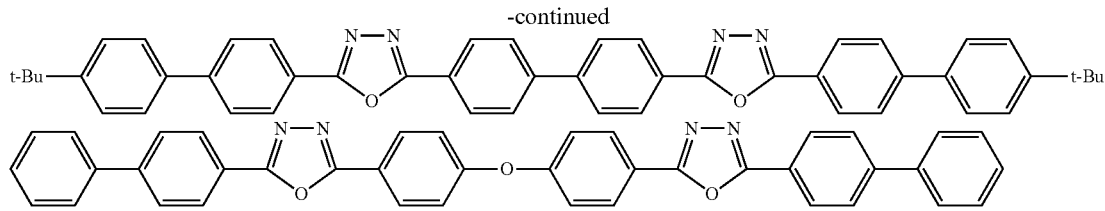

(Me is methyl and tBu is t-butyl.)

Furthermore, as materials used for the electron-injecting layer and electron-transporting layer, the compounds represented by the following formulas (E) to (J) may be used.

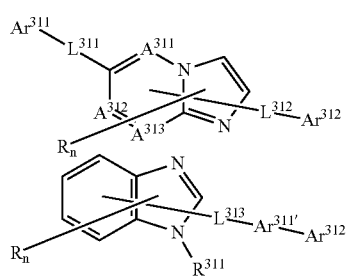

(E)

(F)

Nitrogen-containing heterocyclic derivatives shown by the formulas (E) and (F):

wherein $Ar^{311}$ to $Ar^{313}$ are independently a nitrogen atom or a carbon atom, $Ar^{311}$ is a substituted or unsubstituted aryl group having 6 to 60 ring carbon atoms or a substituted or unsubstituted heteroaryl group having 3 to 60 ring atoms, $Ar^{311'}$ is an arylene group having 6 to 60 ring carbon atoms or a substituted or unsubstituted heteroarylene group having 3 to 60 ring atoms, and $Ar^{312}$ is a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, provided that one of $Ar^{311}$ and $Ar^{312}$ is a substituted or unsubstituted fused ring group having 10 to 60 ring carbon atoms or a substituted or unsubstituted monohetero fused ring group having 3 to 60 ring atoms, $L^{311}$, $L^{312}$ and $L^{313}$ are independently a single bond, a substituted or unsubstituted arylene group having 6 to 60 ring carbon atoms, a substituted or unsubstituted heteroarylene group having 3 to 60 ring atoms, or a substituted or unsubstituted fluorenylene group, R and $R^{311}$ are independently a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, n is an integer of 0 to 5, and when n is two or more, plural Rs may be the same or different, and adjacent Rs may be bonded to each other to form a carbocyclic aliphatic ring or a carbocyclic aromatic ring.

HAr-$L^{314}$-$Ar^{321}$—$Ar^{322}$ (G)

Nitrogen-containing heterocyclic derivatives shown by the formula (G):

wherein HAr is a nitrogen-containing heterocyclic ring having 3 to 40 carbon atoms, which may have a substituent, $L^{314}$ is a single bond, an arylene group having 6 to 60 carbon atoms, which may have a substituent, an heteroarylene group having 3 to 60 atoms, which may have a substituent, or a fluorenylene group which may have a substituent, $Ar^{321}$ is a divalent aromatic hydrocarbon group having 6 to 60 carbon atoms, which may have a substituent, and $Ar^{322}$ is an aryl group having 6 to 60 carbon atoms, which may have a substituent or a heteroaryl group having 3 to 60 atoms, which may have a substituent.

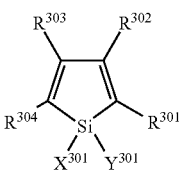

(H)

Silacyclopentadiene derivatives shown by the formula (H) wherein $X^{301}$ and $Y^{301}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or X and Y are bonded to form a saturated or unsaturated ring, and $R^{301}$ to $R^{304}$ are independently hydrogen, halogen, an alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group. These groups may be substituted and adjacent groups may form a substituted or unsubstituted fused ring.

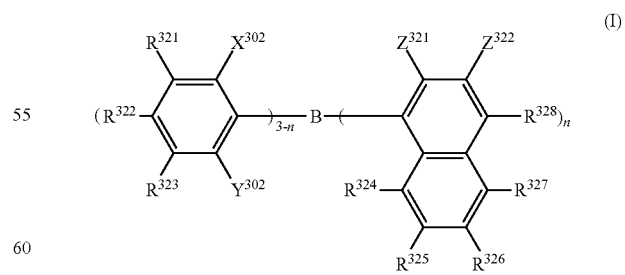

(I)

Borane derivatives shown by the formula (1) wherein $R^{321}$ to $R^{328}$ and $Z^{322}$ are independently a hydrogen atom, a saturated or unsaturated hydrocarbon group, an aromatic hydrocarbon group, a heterocyclic group, a substituted amino group, a substituted boryl group, an alkoxy group, or an aryloxy group, $X^{302}$, $Y^{302}$, and $Z^{321}$ are independently a saturated or unsaturated hydrocarbon group, an aromatic hydrocarbon group, a heterocyclic group, a substituted amino group, an alkoxy group, or an aryloxy group, $Z^{321}$ and $Z^{322}$ may be bonded to form a fused ring, and n is an integer of 1 to 3, provided that when n or (3−n) is two or more, $R^{321}$ to $R^{328}$, $X^{302}$, $Y^{302}$, $Z^{322}$ and $Z^{321}$ may be the same or different, provided that compounds where n is 1, $X^{302}$, $Y^{302}$, and $R^{322}$ are methyl groups, and $R^{328}$ is a hydrogen atom or a substituted boryl group, and compounds where n is 3 and $Z^{321}$ is a methyl group are excluded.

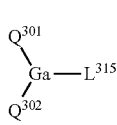

(J)

Gallium complexes shown by the formula (J) wherein $Q^{301}$ and $Q^{302}$ are independently ligands represented by the following formula (K) and $L^{315}$ is a halogen atom, a substituted or unsubstituted alkyl group, a substituted or unsubstituted cycloalkyl group, a substituted or unsubstituted aryl group, a substituted or unsubstituted heterocyclic group, —OR (R is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga—$Q^{303}(Q^{304})$ wherein $Q^{303}$ and $Q^{304}$ are the same as $Q^{301}$ and $Q^{302}$.

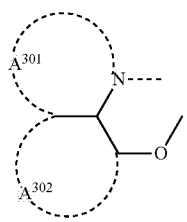

(K)

wherein rings $A^{301}$ and $A^{302}$ are independently a 6-membered aryl ring structure which may have a substituent and they are fused to each other.

The metal complexes have the strong nature of an n-type semiconductor and large ability of injecting electrons. Further, the energy generated at the time of forming a complex is small so that a metal is then strongly bonded to ligands in the complex formed and the fluorescent quantum efficiency becomes large as the emitting material.

Specific examples of the substituents for the rings $A^{301}$ and $A^{302}$ forming the ligand of the formula (K) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, substituted or unsubstituted carbamoyl groups such as a carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and cyclohexyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, and benzimidazolyl group. The above substituents may be bonded to form a further six-membered aryl ring or heterocyclic ring.

A preferred embodiment of the organic EL device is a device containing a reducing dopant in an electron-transferring region or in an interfacial region between a cathode and an organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal carbonates, alkaline earth metal carbonates, rare earth metal carbonates, alkali metal organic complexes, alkaline earth metal organic complexes, and rare earth metal organic complexes.

More specific examples of the preferred reducing dopants include at least one alkali metal selected from the group consisting of Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

An electron-injecting layer made of an insulator or a semiconductor may further be provided between a cathode and an organic layer. By forming the electron-injecting layer, a current leakage can be effectively prevented and electron-injecting properties can be improved. If the electron-injecting layer is an insulating thin film, more uniformed thin film can be formed whereby pixel defects such as a dark spot are decreased.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, CsF, LiCl, KCl and NaCl. Preferable halides of alkaline earth metals include fluorides such as $CaF_2$, $BaF_2$, $SrF_2$, $MgF_2$ and $BeF_2$ and the other halides corresponding to the fluorides.

Semiconductors forming an electron-injecting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-injecting layer is preferably a microcrystalline or amorphous insulating thin film.

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, cesium, magnesium/silver alloy, aluminum/aluminum oxide, $Al/Li_2O$, Al/LiO, Al/LiF, aluminum/lithium alloy, indium, and rare earth metals.

The cathode is formed from these electrode materials by vapor deposition, sputtering or the like.

In the case where emission from the emitting layer is outcoupled through the cathode, it is preferred to make the transmittance of the cathode to the emission larger than 10%. The sheet resistance of the cathode is preferably several hundreds $\Omega/\square$ or less, and the film thickness thereof is usually from 10 nm to 1 μm, preferably from 50 to 200 nm.

Generally, in the organic EL device, pixel defects based on leakage or a short circuit are easily generated since an electric field is applied to the super thin film. In order to prevent this, it is preferred to insert an insulating thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or laminate thereof may be used.

As for the method for fabricating the organic EL device, it can be fabricated by forming necessary layers sequentially from the anode using the materials and the method as mentioned above, and finally forming the cathode. The organic EL device can be fabricated in the order reverse to the above, i.e., the order from the cathode to the anode.

An example of the fabrication of the organic EL device will be described below which has a structure wherein the following are successively formed on a transparent substrate: anode/hole-injecting layer/emitting layer/electron-injecting layer/cathode.

At first, a thin film formed of an anode material is formed on a transparent substrate by vapor deposition or sputtering to form an anode.

Next, a hole-injecting layer is formed on this anode. As described above, the hole-injecting layer can be formed by vacuum deposition, spin coating, casting, LB technique, or some other method. Vacuum deposition is preferred since a homogenous film is easily obtained and pinholes are not easily generated. In the case where the hole-injecting layer is formed by vacuum deposition, conditions for the deposition vary depending upon a compound used (a material for the hole-injecting layer), a desired structure of the hole-injecting layer, and others. In general, the conditions are preferably selected from the following: deposition source temperature of 50 to 450° C., vacuum degree of $10^{-7}$ to $10^{-3}$ Torr, vapor deposition rate of 0.01 to 50 nm/second, and substrate temperature of −50 to 300° C.

Next, an emitting layer is formed on the hole-injecting layer. The emitting layer can also be formed by making a luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-injecting layer.

Next, an electron-injecting layer is formed on the emitting layer. Like the hole-injecting layer and the emitting layer, the layer is preferably formed by vacuum vapor deposition because a homogenous film is required. Conditions for the deposition can be selected from conditions similar to those for the hole-injecting layer and the emitting layer.

Lastly, a cathode is stacked thereon to obtain an organic EL device. The cathode can be formed by vapor deposition or sputtering. However, vapor vacuum deposition is preferred in order to protect underlying organic layers from being damaged when the cathode film is formed.

For the organic EL device fabrication described above, it is preferred that the formation from the anode to the cathode is continuously carried out, using only one vacuuming operation.

The method for forming each of the layers in the organic EL device is not particularly limited. An organic thin film layer containing the compound of the invention can be formed by a known method such as vacuum vapor deposition, molecular beam epitaxy (MBE), or an applying coating method using a solution in which the compound is dissolved in a solvent, such as dipping, spin coating, casting, bar coating, or roll coating.

EXAMPLES

The invention will be specifically explained with reference to examples below.

Synthesis Example 1

Triphenylenyl trifluoromethane sulfonate (intermediate A) was synthesized by the following reaction.

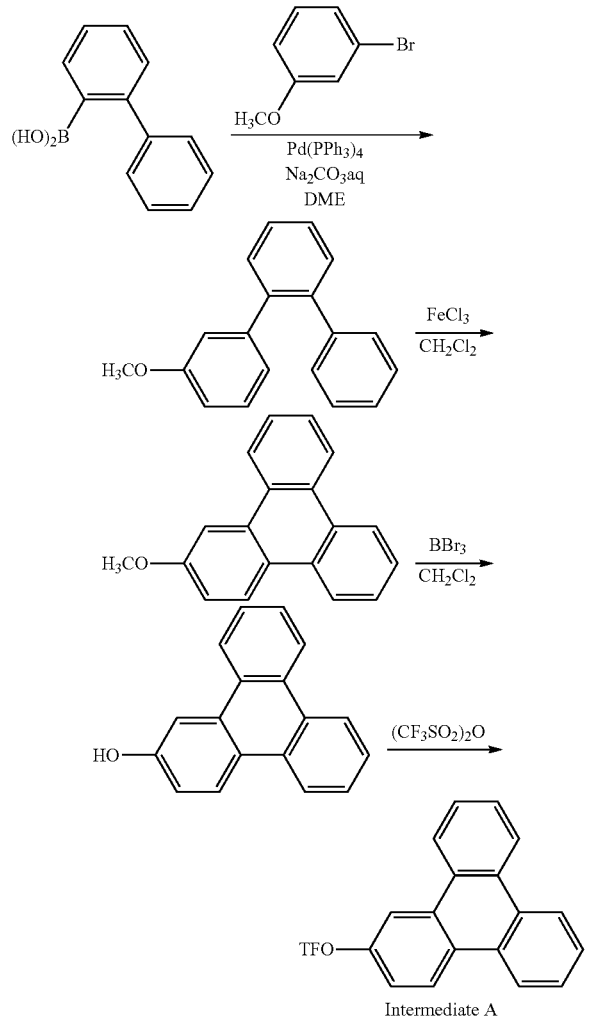

Intermediate A (A-1) Synthesis of 3-methoxy[1,1':2',1"]terphenyl

Under an argon atmosphere, 18.7 g of 3-bromoanisole, 23.8 g of 2-biphenylboronic acid and 2.31 g of tetraxis(triphenylphosphine)palladium(0) were placed in a flask. 340 mL of dimethyl ether (DME) and 170 mL of a 2M aqueous sodium carbonate solution were added to this flask, and the resultant was refluxed with stirring while heating for 8 hours. After cooling to room temperature, an aqueous phase was removed. An organic phase was washed with water and saturated brine, and then dried with magnesium sulfate. After the magnesium sulfate was filtered out, the organic phase was concentrated. The resulting residue was purified by means of silica gel column chromatography, whereby 23.4 g (yield: 90%) of intended 3-methoxy[1,1':2',1"]terphenyl was obtained.

(A-2) Synthesis of 2-methoxytriphenylene 23.4 g of 3-methoxy[1,1':2',1"]terphenyl, 146 g of iron (III) chloride and 200 mL of methylene chloride were placed in a flask, and stirred for one hour while deaerating with argon. The reaction solution was subjected to filtration, followed by washing with an excessive amount of acetone. The resulting solid was dissolved in heated toluene. Insoluble substances were filtered out, followed by crystallization with cooling. The resulting crystal was collected by filtration to obtain 13.9 g (yield: 60%) of 2-methoxytriphenylene.

(A-3) Synthesis of 2-hydroxytriphenylene

Under an argon atmosphere, 13.9 g of 2-methoxytriphenylene was placed in a flask, and 300 mL of methylene chloride was added. The reaction solution was cooled to –78° C., and 54 mL of a solution of 1M boron boron tribromide in methylene chloride was dropwise added thereto. The reaction solution was stirred for 5 hours while increasing temperature of the reaction solution to room temperature. 100 mL of water was added to the reaction solution, followed by filtration. The resulting solid was washed with water and methanol to obtain 12.5 g (yield: 95%) of 2-hydroxytriphenylene.

(A-4) Synthesis of Intermediate A

Under an argon atmosphere, 12.5 g of 2-hydroxytriphenylene and 0.93 g of 4-dimethylaminopiridine were placed in a flask, 200 mL of methylene chloride was added thereto and the reaction solution was cooled to –78° C. 8.22 g of 2,6-dimethylpiridine was added to the reaction solution and then, 17.3 g of trifluoromethanesulfonic acid anhydride was dropwise added thereto. The reaction solution was stirred for 5 hours while increasing temperature of the reaction solution to room temperature. The deposited solid was collected by filtration, washed with water and methanol and then dried to obtain 17.3 g (yield: 90%) of triphenylenyl trifluoromethanesulfonate.

Synthesis Example 2

Synthesis of 2-(3-buromophenyl)triphenylene (Intermediate B)

2-(3-bromophenyl)triphenylene (intermediate B) was synthesized from the intermediate A obtained in Synthesis Example 1 by the following reaction.

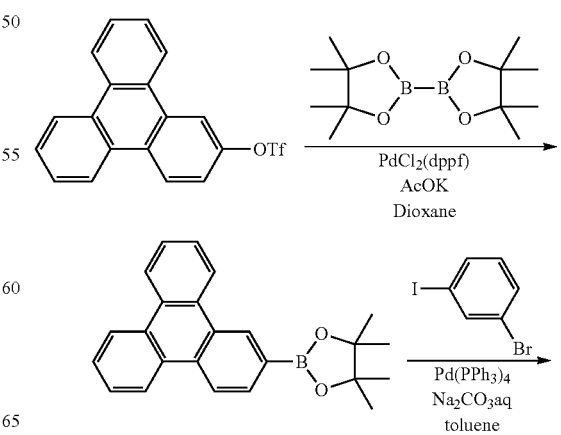

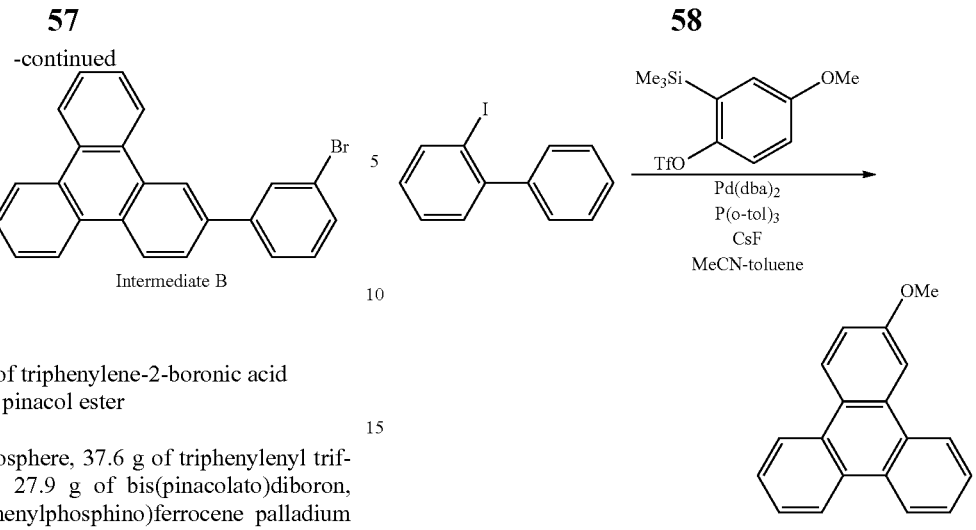

Intermediate B (B-1) Synthesis of triphenylene-2-boronic acid pinacol ester

Under an argon atmosphere, 37.6 g of triphenylenyl trifluoromethanesulfonate, 27.9 g of bis(pinacolato)diboron, 2.45 g of 1,1'-bis(diphenylphosphino)ferrocene palladium (II) dichloride dichloromethane complex, 1.66 g of 1,1'-bis(diphenylphosphino)ferrocene and 29.4 g of potassium acetate were placed in a flask. 600 mL of anhydrous dioxane was added thereto, and the resultant was refluxed with stirring while heating for 8 hours. After cooling to room temperature, 300 mL of water was added to the reaction solution, followed by extraction with toluene. An aqueous phase was removed, and an organic phase was washed with water and saturated brine, and then dried with magnesium sulfate. Magnesium sulfate was removed and the solvent was distilled under reduced pressure. The resulting residue was purified by means of silica gel column chromatography, whereby 14.1 g (yield: 40%) of triphenylene-2-boronic acid picohal ester was obtained.

(B-2) Synthesis of Intermediate B

Under an argon atmosphere, 3.54 g of triphenylene-2-boronic acid piconal ester, 2.83 g of 3-bromoiodebenzene, 0.231 g of tetrakis(triphenylphosphine)palladium (0), 40 mL of toluene and 20 mL of a 2M sodium carbonate aqueous solution were placed in a flask, and refluxed with stirring for 8 hours. After cooling to room temperature, the reaction solution was extracted with toluene. An aqueous phase was removed, and an organic phase was washed with water and saturated brine sequentially, and then dried with magnesium sulfate. Magnesium sulfate was filtered out, and then the organic phase was concentrated. The resulting residue was purified by means of a silica gel column chromatography to obtain 3.64 g (95%) of an intermediate B.

Synthesis Example 3

Synthesis of 2-(4-bromophenyl)triphenylene (Intermediate C)

In (B-2) above, 2-(4-bromophenyl)triphenylene (intermediate C) was synthesized in the same manner as in Synthesis Example 2 except that 4-bromoiodobenzene was used in place of 3-bromoiodobenzen.

Synthesis Example 4

Synthesis of 2-methoxytriphenylene (Intermediate D)

2-methoxytriphenylene (intermediate D) was synthesized by the following reaction.

Under an argon atmosphere, 3.87 mL of 2-iodobiphenyl, 11.52 mL of trifluoromethanesulfonate 4-methoxy-2-(trimethylsilyl)phenyl, 0.63 g of bis(dibenzylideneacetone)palladium, 0.33 g of tri(o-tolyl)phosphine, 270 mL of toluene and 30 mL of acetonitrile were placed in a flask and refluxed with heat while stirring at 110° C. for 6 hours. After completion of the reaction, water was added to the reaction solution. An aqueous phase was removed, and then an organic phase was washed with saturated brine. The organic phase was dried with magnesium sulfate and then concentrated. The resulting residue was purified by means of a silica gel column chromatography to obtain 1.34 g (yield: 23%) of 2-methoxytriphenylene (intermediate D) as a white crystal.

Synthesis of Fused Aromatic Derivatives

Example 1

The following compound 1 was synthesized from intermediate A by the following reaction.

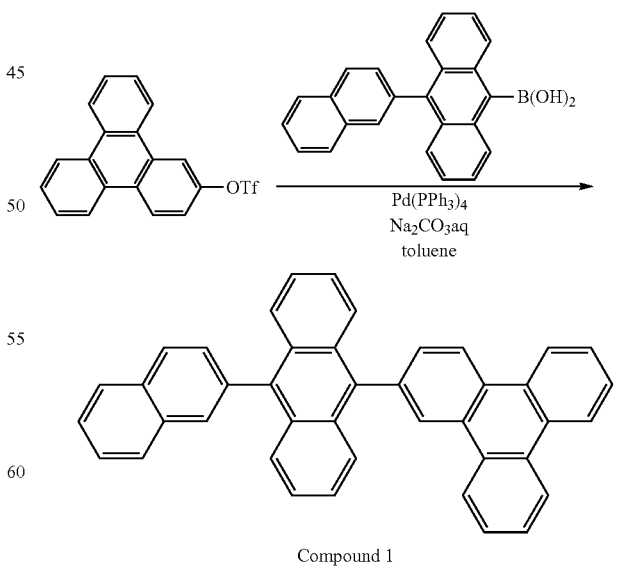

Compound 1

Under an argon atmosphere, 3.76 g of intermediate A obtained in Synthesis Example 1, 4.18 g of 10-(2-naphthyl)

anthracene-9-boronic acid which was synthesized by a known method, 0.231 g of tetrakis(triphenylphosphine)palladium (0), 40 mL of toluene and 20 mL of a 2M sodium carbonate aqueous solution were placed in a flask and refluxed with stirring for 8 hours. After cooling to room temperature, the reaction solution was extracted with toluene. An aqueous phase was removed, and an organic phase was washed with water and saturated brine sequentially and dried with magnesium sulfate. Magnesium sulfonate was filtered out, and then the organic phase was concentrated. The resulting residue was purified by means of a silica gel column chromatography to obtain 4.35 g of a pale yellow crystal.

As a result of mass spectrum analysis, m/z=530, and it was confirmed that the product of the synthesis was Compound 1 (molecular weight: 530.20).

Example 2

The following compound 2 was synthesized by the following reaction.

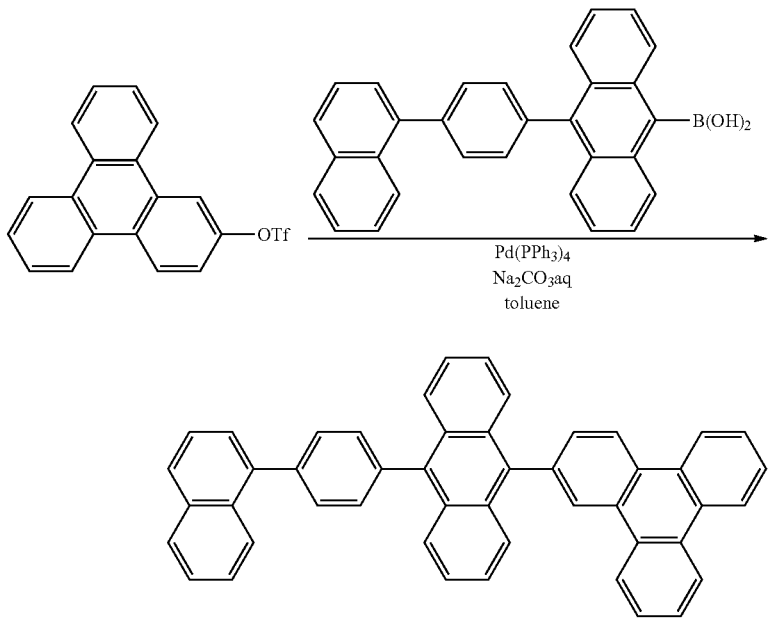

Compound 2

Synthesis was conducted in the same manner as in Example 1 except that 10-[4-(1-naphthyl)phenyl]anthracene-9-boronic acid which was synthesized by a known method was used in place of 10-(2-naphthyl)anthracene-9-boronic acid.

As a result of mass spectrum analysis, m/z=606, and it was confirmed that the product of the synthesis was Compound 2 (molecular weight: 606.23).

Example 3

The following compound 3 was synthesized by the following reaction.

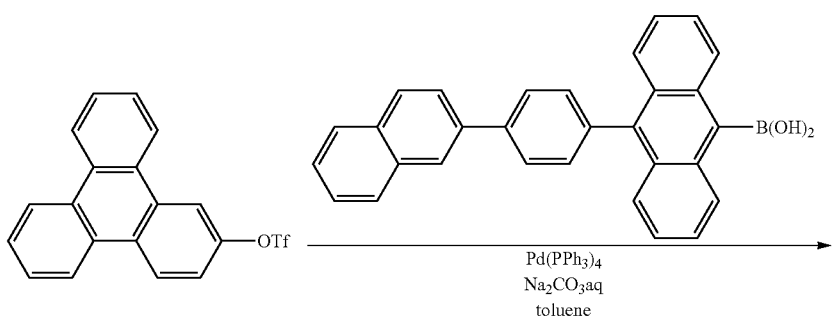

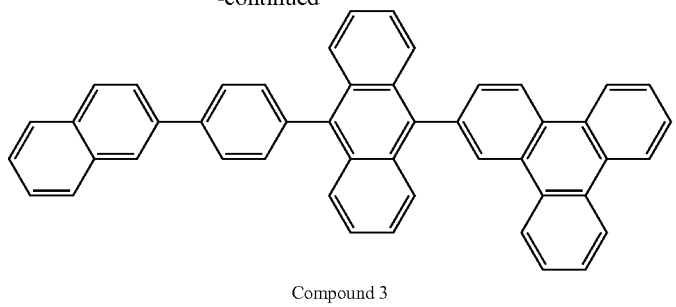

Compound 3

Synthesis was conducted in the same manner as in Example 1 except that 10-[4-(2-naphthyl)phenyl]anthracene-9-boronic acid which was synthesized by a known method was used in place of 10-(2-naphthyl)anthracene-9-boronic acid.

As a result of mass spectrum analysis, m/z=606 and it was confirmed that the product of the synthesis was Compound 3 (molecular weight: 606.23).

Example 4

The following compound 4 was synthesized by the following reaction.

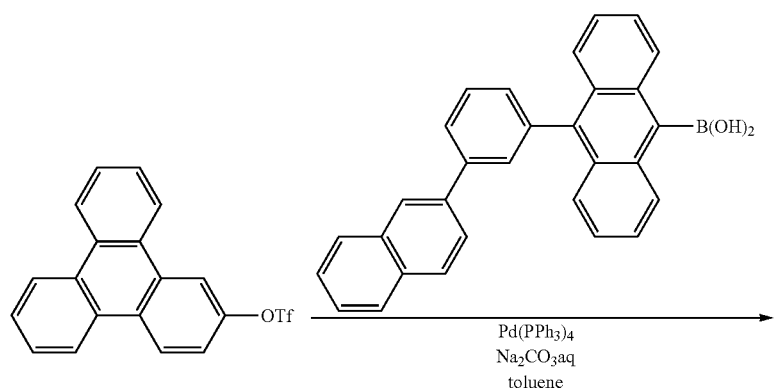

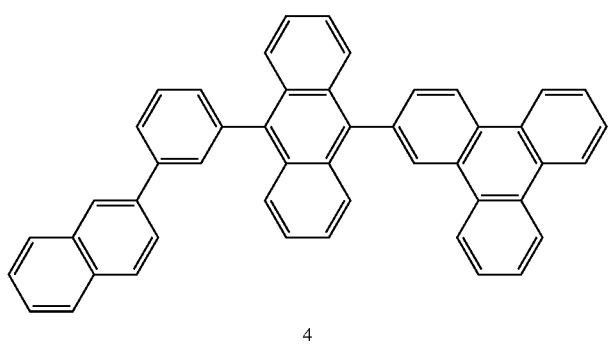

4
Compound 4

Synthesis was conducted in the same manner as in Example 1 except that 10-[3-(2-naphthyl)phenyl]anthracene-9-boronic acid which was synthesized by a known method was used in place of 10-(2-naphthyl)anthracene-9-boronic acid.

As a result of mass spectrum analysis, m/z=606, and it was confirmed that the product of the synthesis was Compound 4 (molecular weight: 606.23).

Example 5

The following compound 5 was synthesized by the following reaction.

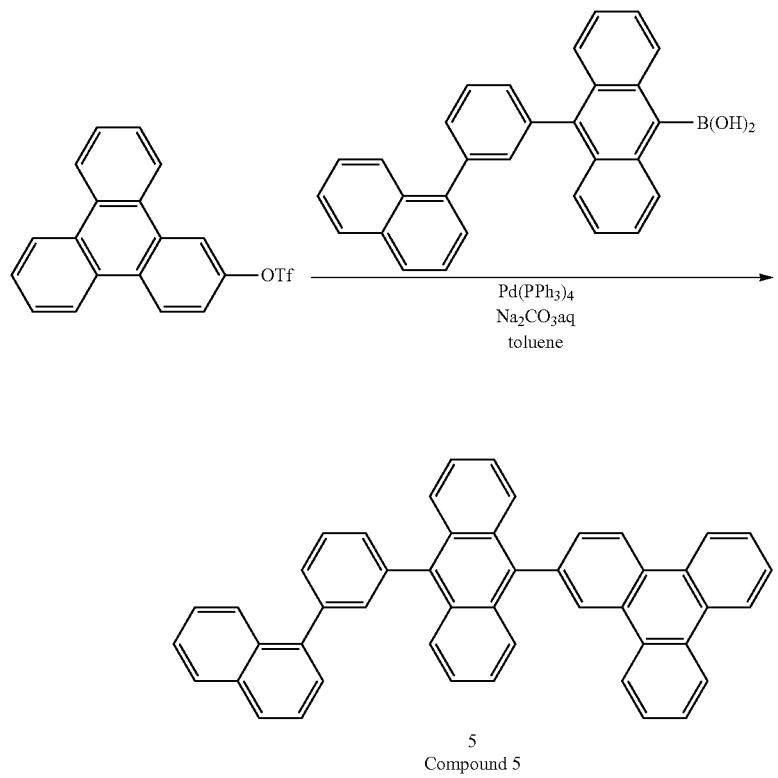

Compound 5

Synthesis was conducted in the same manner as in Example 1 except that 10-[3-(1-naphthyl)phenyl]anthracene-9-boronic acid which was synthesized by a known method was used in place of 10-(2-naphthyl)anthracene-9-boronic acid.

As a result of mass spectrum analysis, m/z=606, and it was confirmed that the product of the synthesis was Compound 5 (molecular weight: 606.23).

Example 6

The following compound 6 was synthesized by the following reaction.

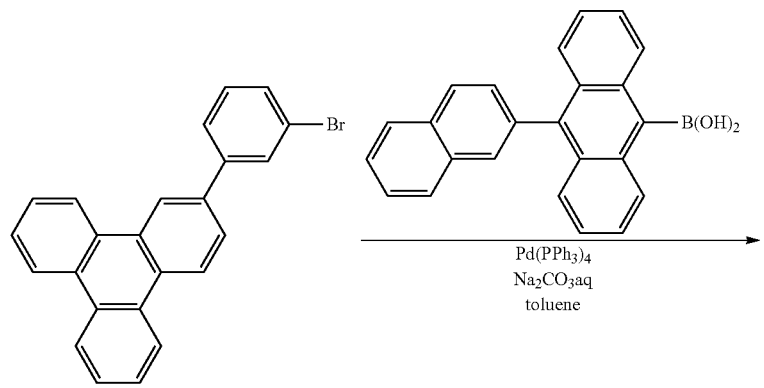

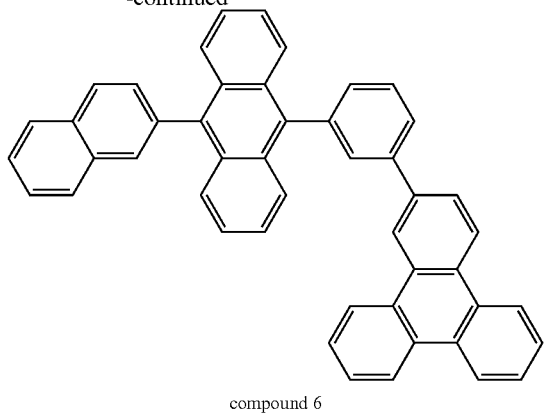
compound 6

Synthesis was conducted in the same manner as in Example 1 except that Intermediate B which was synthesized in Synthesis Example 2 was used in place of triphenylenyl trifluoromethanesulfonate (intermediate A).

As a result of mass spectrum analysis, m/z=606, and it was confirmed that the product of the synthesis was Compound 6 (molecular weight: 606.23).

Example 7

The following compound 7 was synthesized by the following reaction.

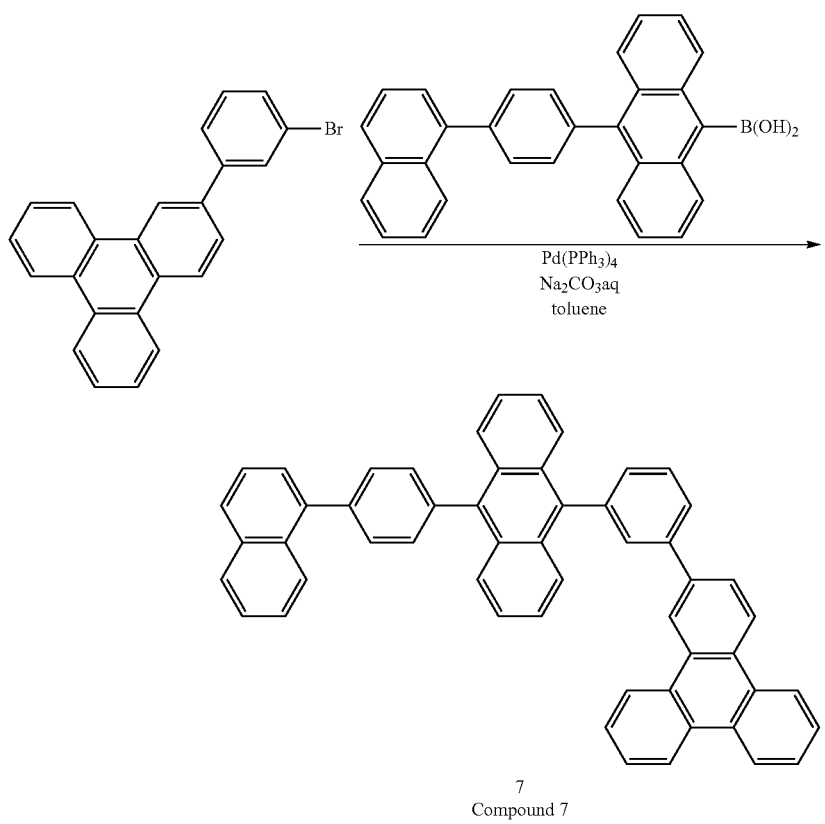

7
Compound 7

Synthesis was conducted in the same manner as in Example 6 except that 10-[4-(1-naphthyl)phenyl]anthracene-9-boronic acid was used in place of 10-(2-naphthyl)anthracene-9-boronic acid.

As a result of mass spectrum analysis, m/z=682, and it was confirmed that the product of the synthesis was Compound 7 (molecular weight: 682.27).

Example 8

The following compound 8 was synthesized by the following reaction.

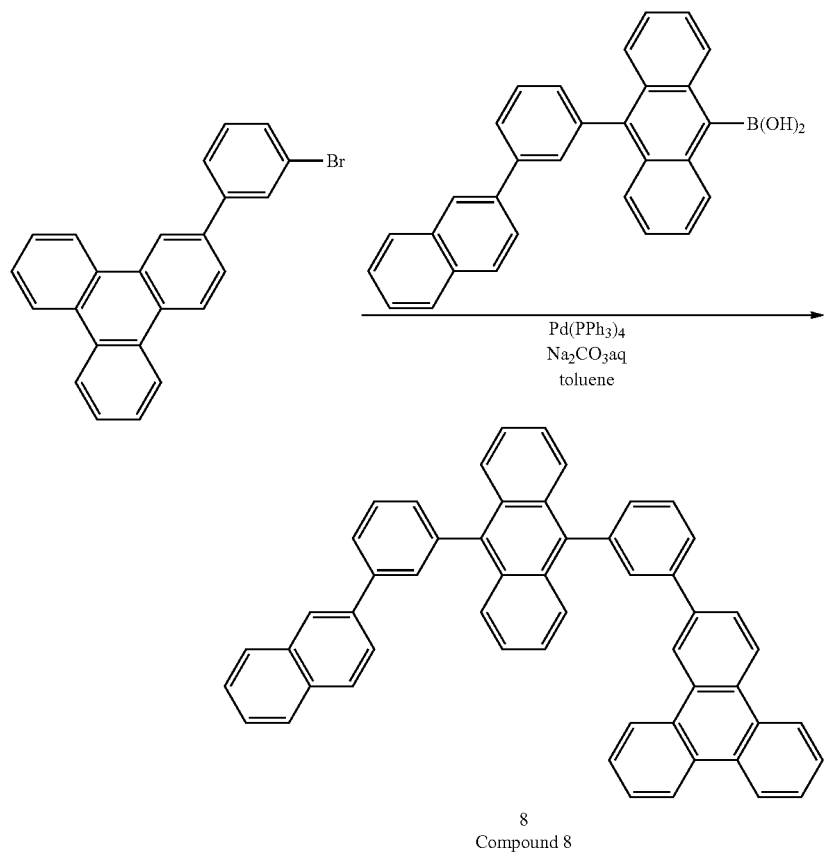

Compound 8

Synthesis was conducted in the same manner as in Example 6 except that 10-[3-(2-naphghyl)phenyl]anthracene-9-boronic acid was used in place of 10-(2-naphthyl)anthracene-9-boronic acid.

As a result of mass spectrum analysis, m/z=682, and it was confirmed that the product of the synthesis was Compound 8 (molecular weight: 682.27).

Example 9

The following compound 9 was synthesized by the following reaction.

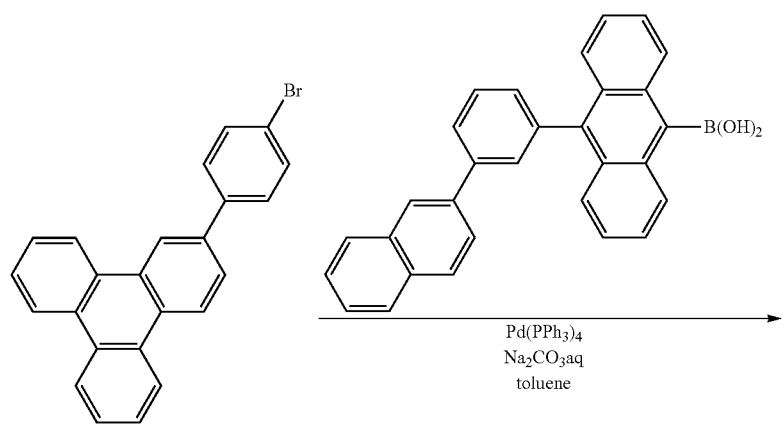

-continued

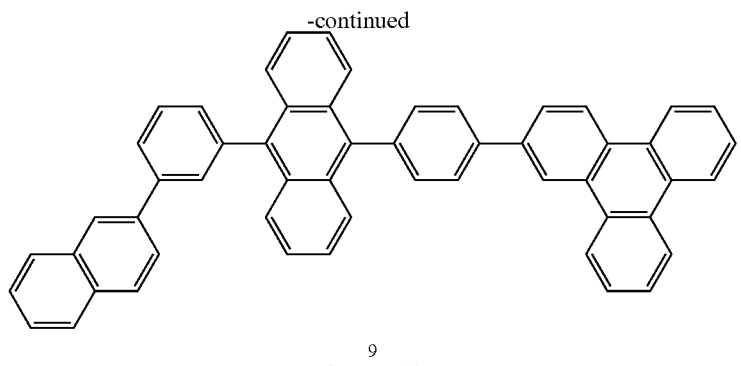

9
Compound 9

Synthesis was conducted in the same manner as in Example 1 except that Intermediate C synthesized in Synthesis Example 3 was used in place of Intermediate A, and 10-[3-(2-naphthyl)phenyl]anthracene-9-boronic acid was used in place of 10-(2-naphthyl)anthracene-9-boronic acid.

As a result of mass spectrum analysis, m/z=682, and it was confirmed that the product of the synthesis was Compound 9 (molecular weight: 682.27).

Fabrication of Organic EL Device

Example 10

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and then cleaned with ultraviolet rays and ozone for 30 minutes. The cleaned glass substrate with transparent electrode lines was mounted in a substrate holder of a vacuum vapor deposition apparatus. First, a 60 nm-thick film of the following compound A-1 was formed on the surface where the transparent electrode lines were formed so as to cover the transparent electrode.

Subsequently to the film formation of A-1 film, a 20 nm-thick film of the following compound A-2 was formed on the A-1 film.

A 40 nm-thick film was formed on the A-2 film using Compound 1 of the invention and a styrylamine derivative D-1 in a film thickness ratio of 40:2, to obtain a blue-light emitting layer.

On this film, a 20 nm-thick film was formed as an electron transporting layer using the following compound Alq by deposition, followed by formation of a 1 nm-thick LiF film. A 150 nm-thick metal Al film was formed on the LiF film by deposition to form a metal cathode, whereby an organic EL device was obtained.

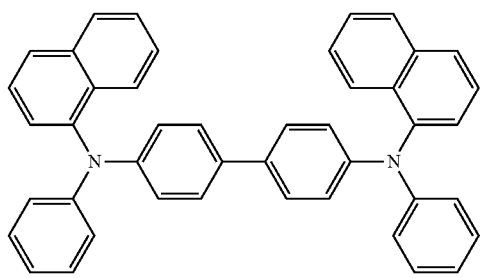

A-2

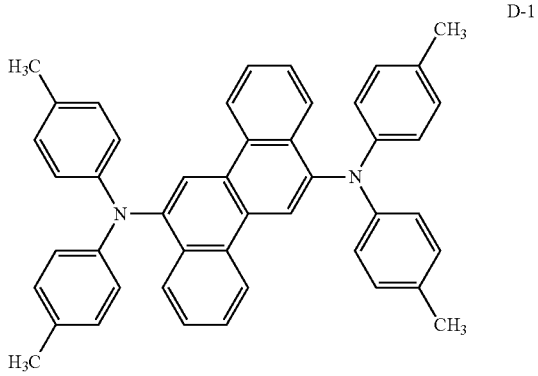

D-1

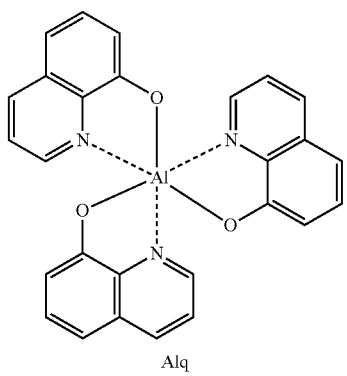

Alq

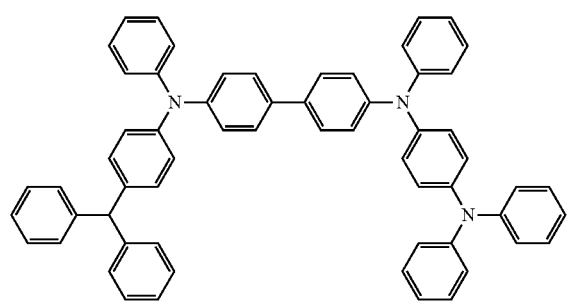

A-1

Examples 11 to 18

As shown in Table 1, organic EL devices were fabricated in the same manner as in Example 10 except that Compounds 2 to 9 were used in place of Compound 1.

Comparative Example 1

An organic EL device was fabricated in the same manner as in Example 10 except that the following compound (B) was used in place of Compound 1.

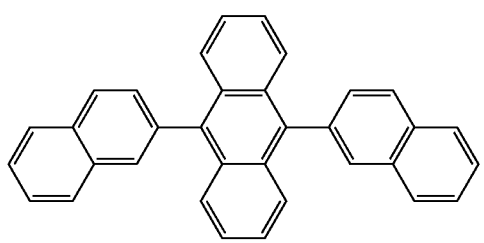

(B)

Comparative Example 2

An organic EL device was fabricated in the same manner as in Example 10 except that the following compound (C) was used in place of Compound 1.

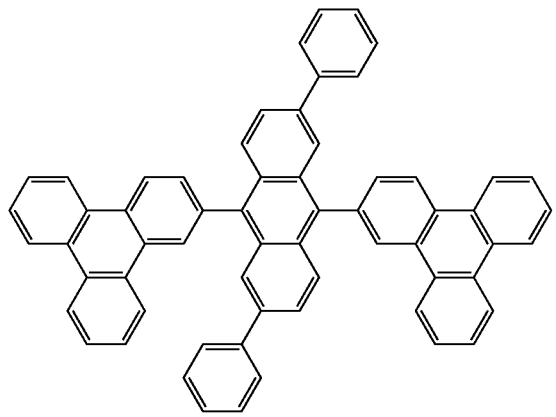

(C)

For the organic EL devices fabricated in each example above, device performance under driven at 10 mA/cm$^2$ and the half life (time) at the initial luminance of 1000 cd/m$^2$ were measured. The results are shown in Table 1.

TABLE 1

|  | Host | Dopant | Luminous efficiency (cd/A) | Half life |
|---|---|---|---|---|
| Ex. 10 | Compound 1 | D-1 | 6.5 | 8000 |
| Ex. 11 | Compound 2 | D-1 | 6.5 | 8000 |
| Ex. 12 | Compound 3 | D-1 | 6.5 | 8000 |
| Ex. 13 | Compound 4 | D-1 | 6.5 | 8000 |
| Ex. 14 | Compound 5 | D-1 | 6.5 | 8000 |
| Ex. 15 | Compound 6 | D-1 | 6.5 | 8000 |
| Ex. 16 | Compound 7 | D-1 | 6.7 | 7000 |
| Ex. 17 | Compound 8 | D-1 | 6.7 | 7000 |
| Ex. 18 | Compound 9 | D-1 | 6.7 | 7000 |
| Comp. Ex. 1 | Compound (B) | D-1 | 6.0 | 4000 |
| Comp. Ex. 2 | Compound (C) | D-1 | 4.2 | 2000 |

Example 19

Synthesis of Compound 10

The following compound 10 was synthesized by the following reaction.

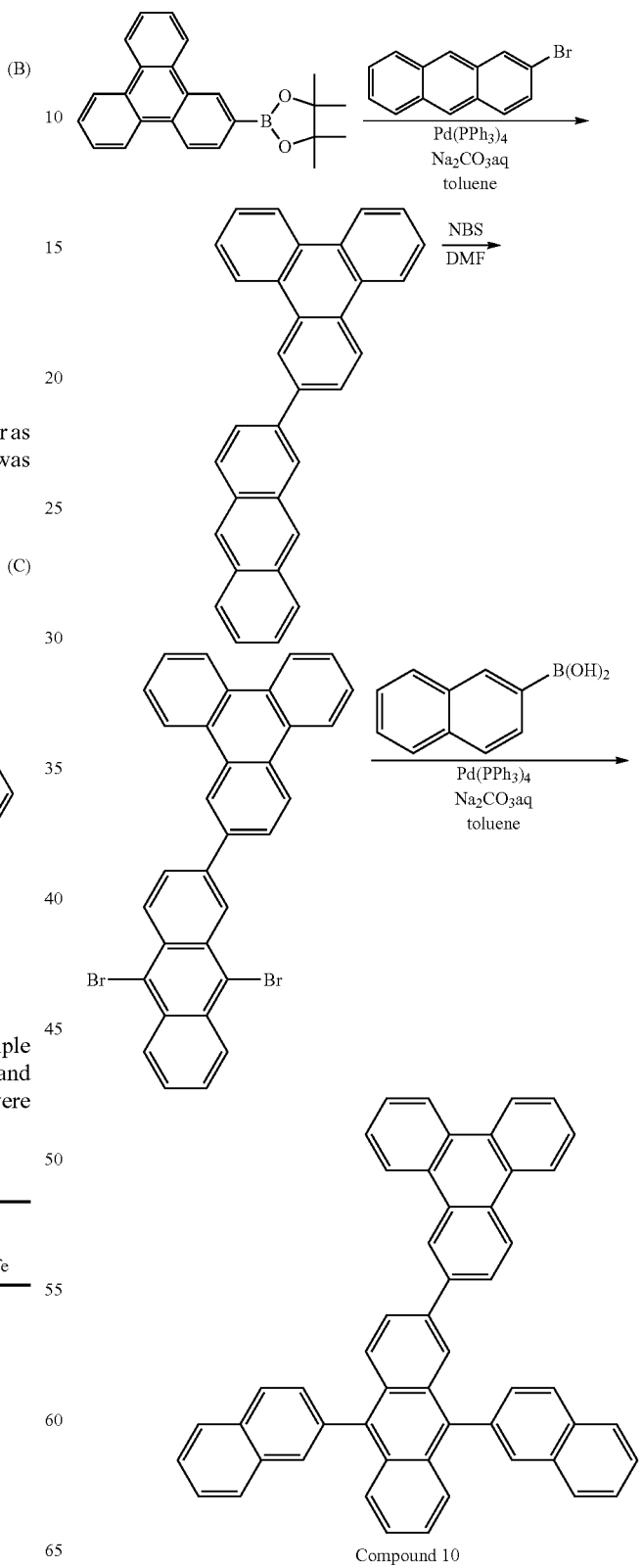

Compound 10

(1) Synthesis of 2-(2-anthryl)triphenylene

Under an argon atmosphere, 7.79 g of triphenylene-2-boronic acid piconal ester, 5.14 g of 2-bromoanthracene, 0.462 g of tetrakis(triphenylphosphine)palladium (0), 30 mL of 1,2-dimethoxyethane and 15 mL of a 2M sodium carbonate aqueous solution were placed in a flask, and refluxed with stirring for 8 hours. After cooling to room temperature, deposited crystals were collected by filtration. The resulting solid was subjected to repeated recrystallization with toluene-hexane and washing to obtain 6.07 g (yield: 75%) of 2-(2-anthryl)triphenylene.

(2) Synthesis of 2-(9,10-dibromoanthracene-2-yl)triphenylene 6.07 g of 2-(2-anthryl)triphenylene was dissolved with heat in 100 mL of N,N-dimethylformamide. A solution of 5.87 g of N-bromosuccinimide in 10 mL of N,N-dimethylformamide was added thereto, and the reaction solution was heated with stirring at 60° C. for 6 hours. After cooling to room temperature, the reaction solution was poured into 1 L of water. The resulting solid was washed with methanol, water and methanol sequentially. Then, recrystallization with toluene-hexane and washing were repeated to obtain 6.75 g (yield: 80%) of 2-(9,10-dibromoanthracene-2-yl)triphenylene.

(3) Synthesis of Compound 10

Under an argon atmosphere, 5.62 g of 2-(9,10-dibromoanthracene-2-yl)triphenylene, 3.78 g of 2-naphthaleneboronic acid, 0.462 g of tetrakis(triphenylphosphin)palladium (0), 40 mL of toluene and 20 mL of a 2M sodium carbonate aqueous solution were placed in a flask and refluxed with stirring for 8 hours. After cooling to room temperature, deposited crystals were collected by filtration. The resulting crystals were washed with methanol, water and methanol, and then recrystallized with toluene to obtain 4.26 g of yellow crystals. As a result of mass spectrum analysis, m/e=656 for the molecular weight of 656.25 of the intended product, and it was confirmed that the compound was the intended product.

Example 20

Synthesis of Compound 11

The following compound 11 was synthesized by the following reaction.

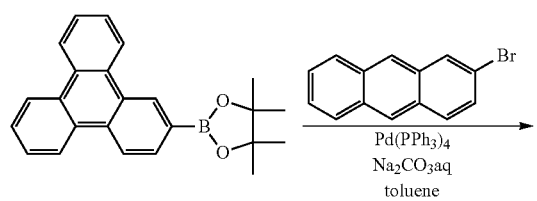

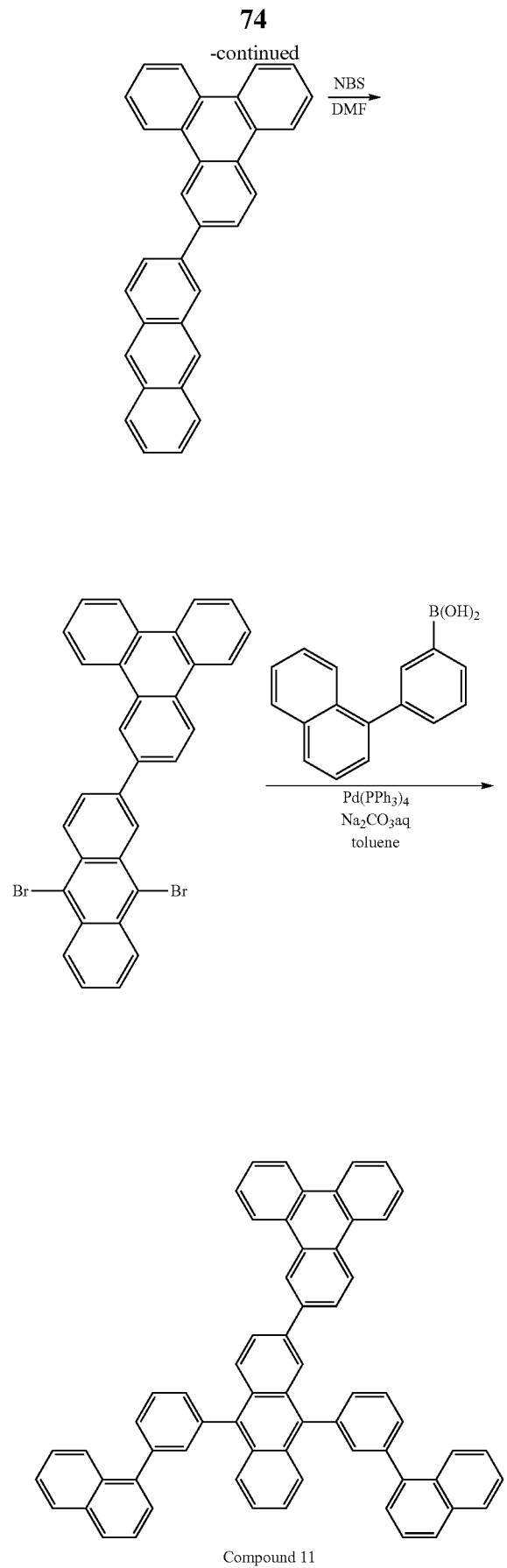

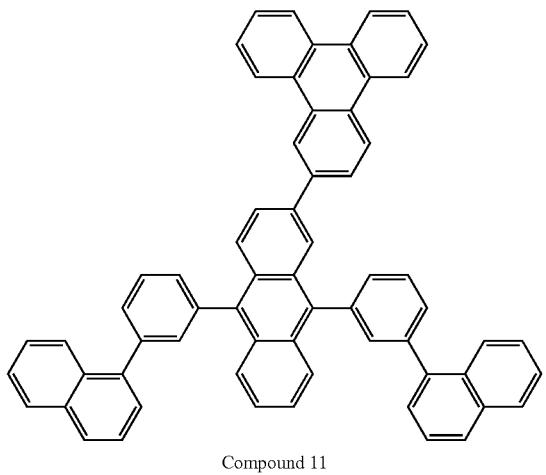

Compound 11

Synthesis was conducted in the same manner as in the synthesis of Compound 10 except that 3-(1-naphthyl)phenylboronic acid which was synthesized by a known method was used in place of 2-naphthareneboronic acid. As a result of mass spectrum analysis, m/e=808 for the molecular weight of the intended product of 808.31, and it was confirmed that the compound was the intended product.

Fabrication of Organic EL Device

Example 21

An organic EL device was fabricated in the same manner as in Example 10 except that a 40 nm-thick film was formed as a blue-color emitting layer using Compound 10 of the invention and Compound D-2 having the following structure in a film thickness ratio of 40:2.

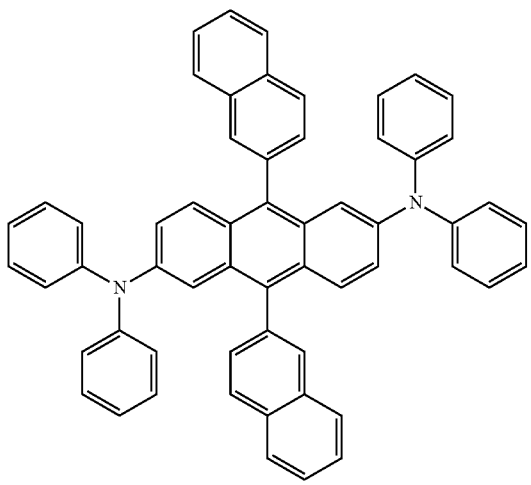

D-2

Example 22

An organic EL device was fabricated in the same manner as in Example 10 except that a 40 nm-thick film was formed as a blue-color emitting layer using Compound 11 of the invention and Compound D-2 in a film thickness ratio of 40:2.

Example 23

An organic EL device was fabricated in the same manner as in Example 21 except that Compound D-3 having the following structure was used in place of Compound D-2.

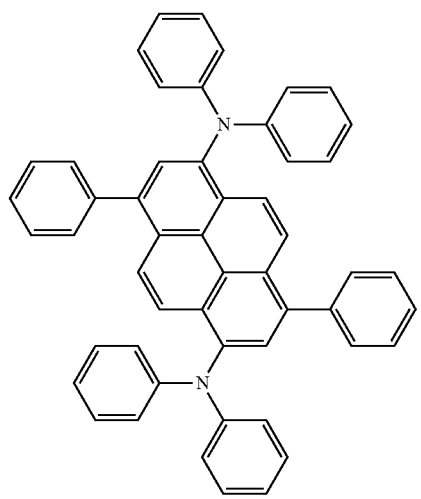

D-3

Example 24

An organic EL device was fabricated in the same manner as in Example 22 except that Compound D-3 was used in place of Compound D-2.

Comparative Example 3

An organic EL device was fabricated in the same manner as in Comparative Example 1 except that Compound D-2 was used in place of Compound D-1.

For the organic EL devices fabricated in each example above, device performance under driven at 10 mA/cm$^2$ and the half life (time) at the initial luminance of 1000 cd/m$^2$ were measured. The results are shown in Table 2.

TABLE 2

| | Host | Dopant | Voltage (V) | Luminous efficiency (cd/A) | Emission color | Half life |
|---|---|---|---|---|---|---|
| Ex. 21 | Compound 10 | D-2 | 6.4 | 22 | Green | 30000 |
| Ex. 22 | Compound 11 | D-2 | 6.5 | 22 | Green | 30000 |
| Ex. 23 | Compound 10 | D-3 | 6.5 | 21 | Green | 50000 |
| Ex. 24 | Compound 11 | D-3 | 6.5 | 21 | Green | 50000 |
| Comp. Ex. 3 | Compound (B) | D-2 | 7.0 | 17 | Green | 10000 |

INDUSTRIAL APPLICABILITY

The fused aromatic ring derivative of the invention is preferable as a material for an organic EL device, in particular, as an emitting material.

The organic EL device of the invention can be suitably used as a light source such as a planar emitting body and backlight of a display, a display part of a portable phone, a PDA, a car navigator, or an instrument panel of an automobile, an illuminator, and the like.

The documents described in the specification are incorporated herein by reference in its entirety.

The invention claimed is:

1. A fused aromatic derivative shown by the following formula (3):

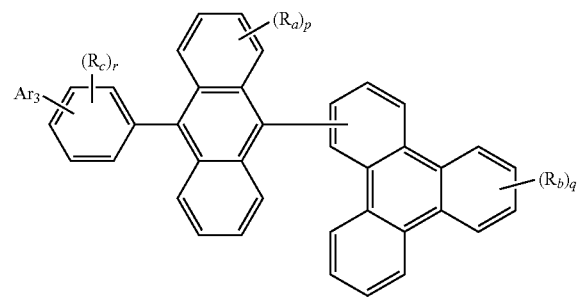

(3)

wherein
$R_a$ and $R_b$ are independently a hydrogen atom or a substituent,
q is an integer of 1 to 11, when q is 2 or more, $R_a$s or $R_b$s may be independently the same or different
$R_c$ is a hydrogen atom or substituent, and
r is an integer of 1 to 4, and when r is two or ore, $R_c$s may be the same or different, and
$Ar_3$ is a substituted or unsubstituted fused aromatic ring having 10 to 20 ring carbon atoms, an aryl-substituted phenyl group shown by the following formula, or a substituted or unsubstituted heteroaryl group having 5 to 50 ring atoms,

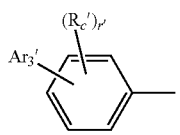

wherein
$R_c'$ is a hydrogen atom or a substituent,
r' is an integer of 1 to 4, and when r' is two or more, each $R_c'$ may be the same or different, and
$Ar_3'$ is a substituted or unsubstituted aryl group having 6 to 50 ring carbon atoms.

2. A fused aromatic derivative shown by the following formula (4):

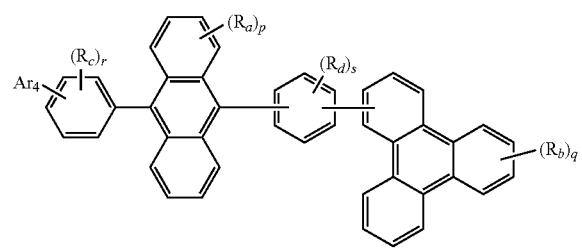

(4)

wherein $R_a$ and $R_b$ are independently a hydrogen atom or a substituent, q is an integer of 1 to 11, when q is 2 or more, $R_a$s or $R_b$s may be independently the same or different,
$R_c$ and $R_d$ are independently a hydrogen atom or a substituent,
r and s are independently an integer of 1 to 4, and when r or s is two or more, $R_c$s or $R_d$s are independently the same or different, and
$Ar_4$ is a substituted or unsubstituted aryl group having 6 to 50 ring carbon atoms or a substituted or unsubstituted heteroaryl group having 5 to 50 ring atoms.

3. The fused aromatic derivative according to claim 2, wherein in the formula (4), $Ar_4$ is a substituted or unsubstituted fused aromatic ring having 10 to 20 ring carbon atoms.

4. A fused aromatic derivative shown by the following formula (5):

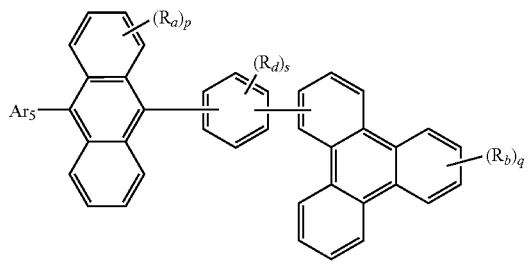

(5)

wherein $R_a$ and $R_b$ are independently a hydrogen atom or a substituent,
q is an integer of 1 to 11, when q is 2 or more, $R_a$s or $R_b$s may be independently the same or different,
$R_d$ is a hydrogen atom or a substituent,
s is an integer of 1 to 4, and when s is two or more, $R_d$s may be the same or different, and
$Ar_5$ is a substituted or unsubstituted fused aromatic group having 10 to 50 ring carbon atoms.

5. The fused aromatic derivative according to claim 4, wherein in the formula (5), $Ar_5$ is a substituted or unsubstituted naphthyl group.

6. A material for an organic electroluminescence device comprising the fused aromatic derivative according to claim 1.

7. The material for an organic electroluminescence derivative according to claim 6, which is an emitting material.

8. An organic electroluminescence device comprising:
an anode, a cathode, and
one or more organic thin film layers comprising an emitting layer between the anode and the cathode,
wherein the emitting layer comprises a fused aromatic derivative shown by the following formula (1) and at least one of a fluorescent dopant and a phosphorescent dopant,

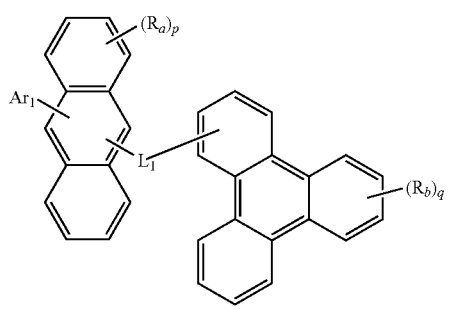

(1)

wherein $R_a$ and $R_b$ are independently a hydrogen atom or a substituent, p is an integer of 1 to 4, and q is an integer of 1 to 11, when p or q is 2 or more, $R_a$s or $R_b$s may be independently the same or different, and adjacent substituents $R_a$s may form a ring, $L_1$ is a single bond, or a substituted or unsubstituted divalent linking group, and $Ar_1$ is a substituted or unsubstituted aryl group having 6 to 50 ring carbon atoms or a substituted or unsubstituted heteroaryl group having 5 to 50 ring atoms, provided that when the triphenylene group bonds to the 9th or 10th position of the anthracene skeleton, $L_1$ is a single bond and at least one of $R_a$s is not a hydrogen, $Ar_1$ is not a triphenylenyl group, and provided that substituents of $L_1$ and $Ar_1$ and $R_a$ and $R_b$ contain no amino group.

9. The organic electroluminescence device according to claim 8, wherein the fluorescent dopant is an arylamine compound.

10. The organic electroluminescence device according to claim 8, wherein the fluorescent dopant is a styrylamine compound.

11. A material for an organic electroluminescence device comprising the fused aromatic derivative according to claim 2.

12. The material for an organic electroluminescence derivative according to claim 11, which is an emitting material.

13. A material for an organic electroluminescence device comprising the fused aromatic derivative according to claim 4.

14. The material for an organic electroluminescence derivative according to claim 13, which is an emitting material.

* * * * *